US006096304A

United States Patent [19]

McCutchen

[11] Patent Number: 6,096,304

[45] Date of Patent: Aug. 1, 2000

[54] RECOMBINANT BACULOVIRUS INSECTICIDES

[75] Inventor: Billy Fred McCutchen, Wilmington, Del.

[73] Assignee: E. I. du Pont de Nemours and Company, Wilmington, Del.

[21] Appl. No.: 08/952,383

[22] PCT Filed: May 16, 1996

[86] PCT No.: PCT/US96/06988

§ 371 Date: Nov. 13, 1997

§ 102(e) Date: Nov. 13, 1997

[87] PCT Pub. No.: WO96/36712

PCT Pub. Date: Nov. 21, 1996

Related U.S. Application Data

[63] Continuation-in-part of application No. 08/443,294, May 17, 1995, abandoned.

[51] Int. Cl.[7] .......................... A61K 48/00; C12N 15/86; C07H 21/04

[52] U.S. Cl. .................... 424/93.2; 424/93.6; 435/320.1; 536/23.4; 536/23.5; 536/24.1

[58] Field of Search ............................... 435/69.1, 235.1, 435/320.1, 5, 6, 91.1, 91.4, 455, 456, 348; 536/23.1, 23.4, 23.5, 23.7, 23.72, 24.1; 424/93.2, 93.6

[56] References Cited

U.S. PATENT DOCUMENTS 5,770,192  6/1998  Cayley et al. ........................ 424/93.2

FOREIGN PATENT DOCUMENTS

| | | |
|---|---|---|
| 0 431 829 | 6/1991 | European Pat. Off. . |
| 0 505 207 | 9/1992 | European Pat. Off. . |
| 0 621 337 | 10/1994 | European Pat. Off. . |
| WO 92/11363 | 7/1992 | WIPO . |

OTHER PUBLICATIONS

Zhang et al., Gene, vol. 105, pp. 61–72, 1991.

*Primary Examiner*—David Guzo

[57] ABSTRACT

This invention pertains to recombinant baculoviruses that have been engineered to afford optimal expression of genes encoding insect-selective neurotoxins. More specifically, this invention pertains to an isolated nucleic acid sequence encoding the scorpion toxin LqhIT2, derived from *Leiurus quinquestriatus hebraeus*, wherein the sequence has been optimized for gene expression in nuclear polyhedrosis virus-infected cells. This invention also pertains to chimeric genes comprising a codon-optimized LqhIT2 nucleotide sequence, insecticidal compositions comprising recombinant baculoviruses expressing a codon-optimized, insect-selective neurotoxin (e.g. the LqhIT2 toxin gene), and methods for controlling insects in both agronomic and non-agronomic environments comprising application of insect baculoviruses containing the codon-optimized nucleic acid sequence encoding an insect-selective neurotoxin such as the LqhIT2 toxin.

12 Claims, 7 Drawing Sheets

FIG. 1

| | | | | | |
|---|---|---|---|---|---|
| LqhIT NPV | GACGGCTACA | TCAAACGCCG | CGACGGCTGC | AAAGTGGCCT | 40 |
| LqhIT cDNA | GACGGATATA | TAAAAAGACG | AGACGGATGC | AAGGTTGCAT | 40 |
| LqhIT NPV | GCCTTATCGG | CAACGAGGGC | TGCGACAAAG | AGTGCAAGGC | 80 |
| LqhIT cDNA | GCCTGATCGG | AAATGAGGGC | TGCGATAAAG | AATGCAAAGC | 80 |
| LqhIT NPV | CTACGGCGGC | AGCTACGGCT | ACTGCTGGAC | CTGGGGCCTC | 120 |
| LqhIT cDNA | TTATGGTGGC | TCTTATGGAT | ATTGTTGGAC | CTGGGGACTT | 120 |
| LqhIT NPV | GCATGCTGGT | GCGAGGGCCT | CCCCGACGAC | AAAACCTGGA | 160 |
| LqhIT cDNA | GCCTGCTGGT | GCGAAGGTCT | TCCGGATGAC | AAGACATGGA | 160 |
| LqhIT NPV | AAAGCGAAAC | CAACACCTGC | GGCTAA | | 186 |
| LqhIT cDNA | AGAGTGAAAC | AAACACATGC | GGTTAA | | 186 |

Lq1
5'- ACGATGAATT CGGATCCTAT GAAGATCCTC CTTGCTATTG CCCTTATGCT TAGCACCGTG  60
    ATGTGGGTGA GCACC - 3'                                              75

Lq2
5'- GACGGCTACA TCAAACGCCG CGACGGCTGC AAAGTGGCCT GCCTTATCGG C - 3'      51

Lq3
5'- AACGAGGGCT GCGACAAAGA GTGCAAAGCC TACGGCGGCA GCTACGGCTA C - 3'      51

Lq4
5'- TGCTGGACCT GGGGCCTCGC ATGCTGGTGC GAGGGCCTCC CCGACGACAA A - 3'      51

Lq5
5'- ACCTGGAAAA GCGAGACCAA CACCTGCGGC TAAGGATCCT CTAGAGTC - 3'          48

Lq6
5'- CACCCACATC ACGGTGCTAA GCATAAGGGC AATAGCAAGG AGGATCTTCA TAGGATCCGA  60
    ATTCATCGT - 3'                                                     69

Lq7
5'- AAGGCAGGCC ACTTTGCAGC CGTCGCGGCG TTTGATGTAG CCGTCGGTGC T - 3'      51

Lq8
5'- GTAGCTGCCG CCGTAGGCTT TGCACTCTTT GTCGCAGCCC TCGTTGCCGA T - 3'      51

Lq9
5'- GTCGGGGAGG CCCTCGCACC AGCATGCGAG GCCCCAGGTC CAGCAGTAGC G - 3'      51

Lq10
5'- GACTCTAGAG GATCCTTAGC CGCAGGTGTT GGTCTCGCTT TTCCAGGTTT TGTC - 3'   54

SYNTHETIC LqhIT2 GENE

```
       Lq1
5' ─────✗─────▶ ─────▶ ─────▶ ─────▶ ─────▶ 3'

3' ◀───── ◀───── ◀───── ◀───── ◀─────✗───── 5'
                                      Lq10
```

A) PHOSPHORYLATE

B) ANNEAL

C) LIGATE

D) PCR

| | −57 | +1 | | | | |
|---|---|---|---|---|---|---|
| 5' | Lq1 | Lq2 | Lq3 | Lq4 | Lq5 | 5' |
| 3' | Lq6 | Lq7 | Lq8 | Lq9 | Lq10 | 3' |
| XbaI / BamHI | | | | | SphI | BamHI / EcoRI |

FIG. 4

LqhIT Seq I.D. # 13 -> 1-phase Translation

DNA sequence  243 b.p.  atgaagatcctc ... ACCTGGGGCTAA  linear

```
1/1                                                  31/11
atg aag atc ctc ctt gct att gcc ctt atg ctt agc acc gtg atg tgg gtg atg acc GAC
 M   K   I   L   L   A   I   A   L   M   L   S   T   V   M   W   V   M   T   D
61/21                                                91/31
GGC TAC ATC AAA CGC CGC GAC GGC TGC AAA GTG GCC TGC CTT ATC GGC AAC GAG GGC TGC
 G   Y   I   K   R   R   D   G   C   K   V   A   C   L   I   G   N   E   G   C
121/41                                               151/51
GAC AAA GAG TGC AAG GCC TAC GGC AGC GGC TAC TGC TGG ACC TGG W T L  G  L  A
 D   K   E   C   K   A   Y   G   S   G   Y   C   W   T   W   G   L   A
181/61                                               211/71
TGC TGG TGC GAG GGC CTC CCC GAC GAC AAA ACC TGG AAA AGC GAA ACC AAC ACC TGC GGC
 C   W   C   E   G   L   P   D   D   K   T   W   K   S   E   T   N   T   C   G
241/81
TAA
  *
```

FIG. 7

% PROTECTION

- WtAcNPV: 63.6
- AcAaIT: 82.2
- AcLqhIT: 92.1
- Control: 100

VIRAL TREATMENTS

RECOMBINANT BACULOVIRUS INSECTICIDES

This application is a 371 application of PCT/US96/06988, filed May 16, 1996, which is a continuation in part of Ser. No. 08/443,294, filed May 17, 1995, now abandoned.

BACKGROUND OF THE INVENTION

Chemical insecticides are an integral component of modem agriculture, and have afforded an effective means for reducing crop damage by controlling insect pests. However, chemical agents are under continuous scrutiny due to the potential for environmental contamination, selection of resistant populations of agronomic pests, and toxicity to non-target organisms such as beneficial insects, aquatic organisms, animals and man. As a result, alternative strategies for insect control are being sought that are effective and yet benign to non-target populations and the environment. One of these strategies comprises the use of microorganisms that are naturally occurring pathogens of target insect populations. However, many candidate entomopathogens that would be promising insect control agents lack the properties of classical chemical insecticides that farmers and others in agribusiness have grown accustomed to. For instance, insect-specific viruses from the family Baculoviridae possess several favorable attributes, including host-specificity and inert environmental properties, but lack the ability to rapidly control a target population before significant crop damage takes place. Fortunately, modern molecular biology provides the tools necessary to favorably modify many of these properties in order to satisfy the needs of modern agriculture.

Baculoviruses are viruses pathogenic to invertebrates, and are characterized by possession of a double-stranded, circular DNA genome ranging in size from 80 to 200 kilobases. Baculoviruses are divided into three subfamilies, including non-occluded baculoviruses (NOVs), granulosis viruses (GVs) and nuclear polyhedrosis viruses (NPVs). Examples of NOVs are *Orcytes rhinoceros* NOV and *Helicoverpa zea* NOV. Examples of GVs include *Plutella xylostella* GV, *Cydia pomonella* GV, *Pieris brassicae* GV, and *Trichoplusia ni* GV. Examples of NPVs include *Autographa californica* NPV, *Spodoptera exigua* NPV, *Heliothis armigera* NPV, *Helicoverpa zea* NPV, *Spodoptera frugiperda* NPV, *Trichoplusia* NPV, *Mamestra brassicae* NPV, *Lymantria dispar* NPV, *Spodoptera litturalis* NPV, *Syngrapha facifera* NPV, *Choristoneura fumiferana* NPV, *Anticarsia gemmatalis* NPV, and *Heliothis virescens* NPV.

Although certain GVs and NOVs have been carefully studied, NPVs are the most thoroughly characterized of the baculovirus subfamilies. The infection cycle of NPVs involves two types of virions. Following infection of insect cells, budded virions (BVs or extra cellular virus, ECV) are produced upon movement of nucleocapsids to the plasma membrane. These virions shed their nuclear-derived coat in the cytoplasm and bud through the cytoplasmic membrane into the hemocoel of the insect host. This process leads to systemic infection of the host insect. Later in the infection process, virions become occluded (occluded virions) within a protein matrix consisting substantially of the polyhedrin protein, thus forming polyhedrin inclusion bodies (PIBs or occlusion bodies, OBs). These inclusion bodies are the orally infectious form of the virus, and provide for horizontal transmission of the virus between insect hosts (1,2). Uninfected larvae feed on virus-contaminated substrates and ingest PIBs. The proteinaceous matrix is solubilized by the action of the basic pH of the insect midgut found in many lepidopterous larvae. The liberated virion nucleocapsids, containing the viral DNA genome, attach to and infect the epithelial cells of the larval midgut. Typically, the infected insect will continue to develop and consume plant material while the virus exponentially propagates within the host. Eventually, often after several weeks or longer have passed, the infected larvae will become filly involved and expire.

An attractive attribute of baculoviruses is their narrow host specificity. These viruses infect only arthropods, and possess relatively narrow host ranges even within a particular insect order. Host specificity has been examined by electron microscopy, DNA hybridization and recombinant DNA technology (3–5). These studies indicate that the narrow host range is due, at least in part, to the inability of baculoviruses to transfer viral DNA into the manalia cell nucleus.

Due in part to the availability of efficient cell culture systems and facile cloning vectors, NPVs have been utilized as eukaryotic expression vectors for synthesis of desirable heterologous proteins (6,7). One virus in particular, *Autographa californica* NPV (AcNPV), is the accepted model virus utilized for introduction and expression of heterologous genes in baculovirus expression systems. Although this virus is routinely used as an important in vitro means of providing for high yields of recombinant proteins in a eukaryotic expression system, thus affording appropriate post-translational modification of expressed proteins, AcNPV is capable of infecting many families of Lepidopteran insects that are important economic pests.

In spite of the potential practical advantages of baculovirus-based pest control agents, a variety of disadvantages have curtailed their use in modern agriculture. The most significant barrier to more widespread use of these viruses in row-crop agriculture is the significant time delay between their application and effective control of crop damage caused by the host insects. Unlike the rapid effects observed upon application of classical chemical insecticides, effective wild-type baculovirus-mediated insect control occurs only after in vivo populations of virus have reached levels high enough to compromise host activity. However, through the use of recombinant DNA technology, NPVs have been genetically engineered to increase their rate of insect killing by either the introduction of genes directing the expression of insecticidal proteins, or deletion of genes from the viral genome (8–10). The most effective recombinant NPVs have been engineered to express insect-selective neurotoxins (11–18). These recombinant viruses kill their hosts in 20–30% less time than wild-type NPVs.

There has now been constructed recombinant NPVs that have significantly greater potency than previously constructed recombinant NPVs. These recombinant NPVs have been engineered to express a heterologous gene encoding the insect-selective toxin LqhIT2 of the scorpion *Leiurus quinquestriatus hebraeus* (19,20). Based on present studies, the recombinant NPVs carrying this synthetic gene provide for a significant increase in the insecticidal properties of the virus.

SUMMARY OF THE INVENTION

This invention pertains to recombinant baculoviruses that have been engineered to afford optimal expression of genes encoding insect-selective neurotoxins. More specifically, this invention pertains to an isolated nucleic acid sequence encoding the scorpion toxin LqhIT2, derived from *Leiurus quinquestriatus hebraeus*, wherein said sequence has been optimized for gene expression in nuclear polyhedrosis virus-infected cells. This invention also pertains to chimeric genes comprising a codon-optimized LqhIT2 nucleotide sequence, insecticidal compositions comprising recombinant baculoviruses expressing a codon-optimized, insect-selective neurotoxin such as the LqhIT2 toxin gene, and methods for controlling insects in both agronomic and non-agronomic environments comprising application of insect baculoviruses containing a codon-optimized, insect-selective neurotoxin such as the LqhIT2 toxin gene.

The insect baculoviruses of the instant invention are selected from the group nuclear polyhedrosis viruses, singly or multiply occluded nuclear polyhedrosis viruses and granulosis viruses. Preferred baculoviruses are selected from the group multinucleocapsid nuclear polyhedrosis viruses. Specifically preferred is *Autographa californica* multinucleocapsid nuclear polyhedrosis virus (AcMNPV).

The instant invention comprises a synthetic gene encoding the LqhIT2 protein wherein codon selection is biased towards codons favored by nuclear polyhedrosis viruses and cells that support their replication, as determined by observation of codon utilization in genes encoding a well characterized nuclear polyhedrosis virus protein, polyhedrin, and several lepidopteran proteins. The resulting genetic constructs afford efficient expression of LqhIT2 in cells infected with recombinant baculoviruses harboring the synthetic LqhIT2 gene. Application of these recombinant viruses to *Heliothis virescens* results in rapid paralysis of treated larvae. Moreover, viruses containing the codon-biased gene kill their insect hosts more rapidly than viruses containing a complimentary DNA (cDNA) copy of the LqhIT2 gene.

BRIEF DESCRIPTION OF THE DRAWINGS

BIOLOGICAL DEPOSITS AND SEQUENCE LISTING

FIG. 1. Alignment of the cDNA sequence of the LqhIT2 gene from *Leiurus quinquestriatus hebraeus* (LqhIT cDNA) and the codon-biased, synthetic structural gene encoding LqhIT2 (LqhIT NPV). Bold letters indicate silent nucleotide changes to the cDNA sequence that were introduced in order to facilitate gene expression.

FIG. 2. Sequence of the synthetic oligonucleotides used to construct the codon-biased form of the LqhIT2 gene. Oligonucleotide Lq1 encodes the Bombyxin signal peptide. Oligonucleotides Lq1 and Lq10 were used as primers for PCR amplification of the synthetic gene.

FIG. 3. Diagrammatic representation of the strategy employed for preparation of the codon-biased form of the LqhIT2 gene. Oligonucleotides Lq1 and Lq10 (marked with an "X") served as amplification primers for PCR reactions. Unique restriction enzyme cleavage sites are indicated.

FIG. 4. Nucleotide and corresponding amino acid sequences of the codon-biased LqhIT2 gene. Lower case letters in the nucleotide sequence (nucleotides 1–57, encoding amino acids 1–19) indicate nucleotides encoding the Bombyxin signal peptide.

Figure 5:
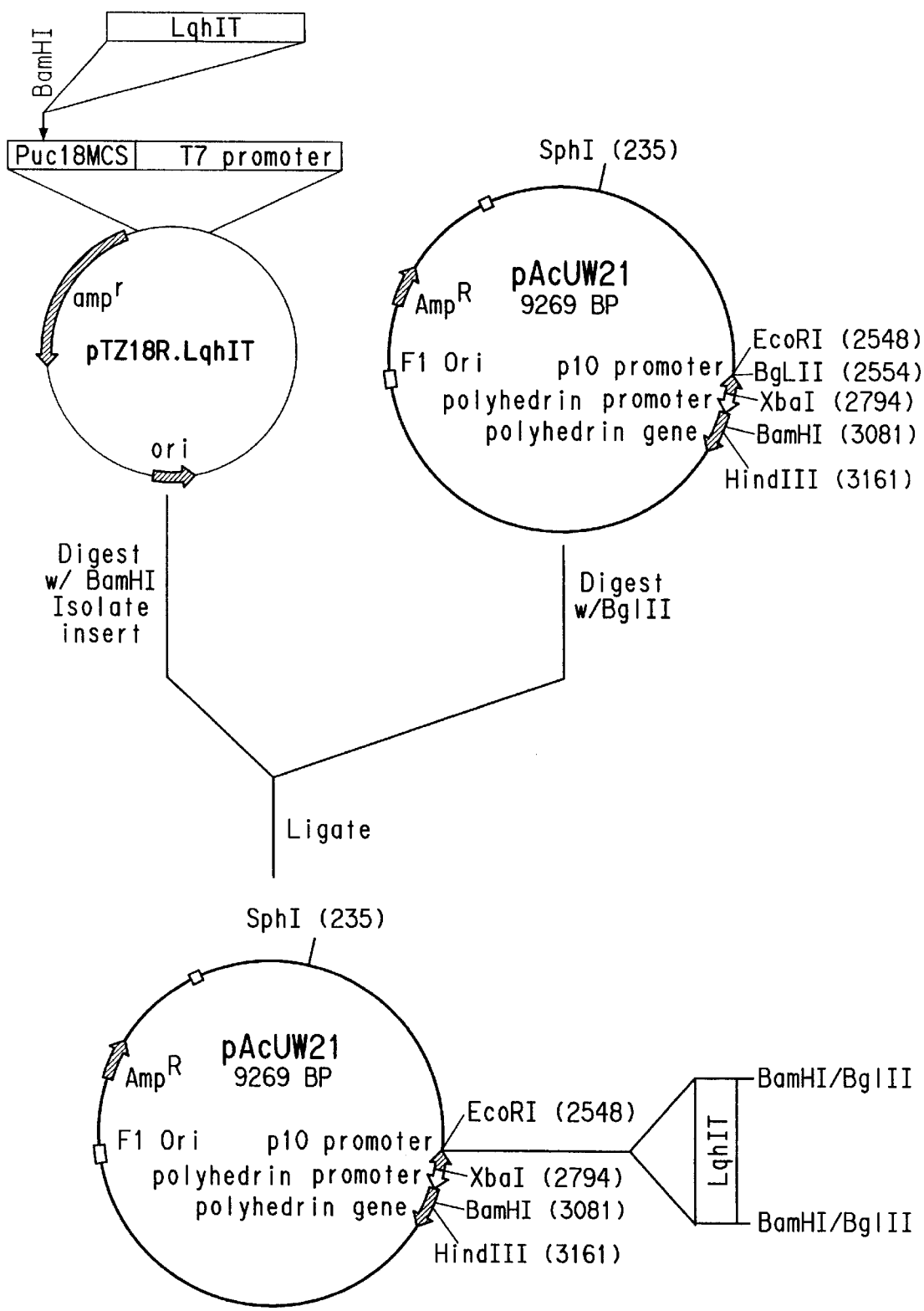

FIG. 5. Plasmid maps of pTZ18R.LqhIT2 (intermediate cloning vector comprising the synthetic, codon-biased LqhIT2 gene), pAcUW21 (the baculovirus transfer vector), and derivation of the plasmid pAcUW21.LqhIT2, a baculovirus transfer vector comprising the synthetic, codon-biased LqhIT2 gene.

Figure 6:
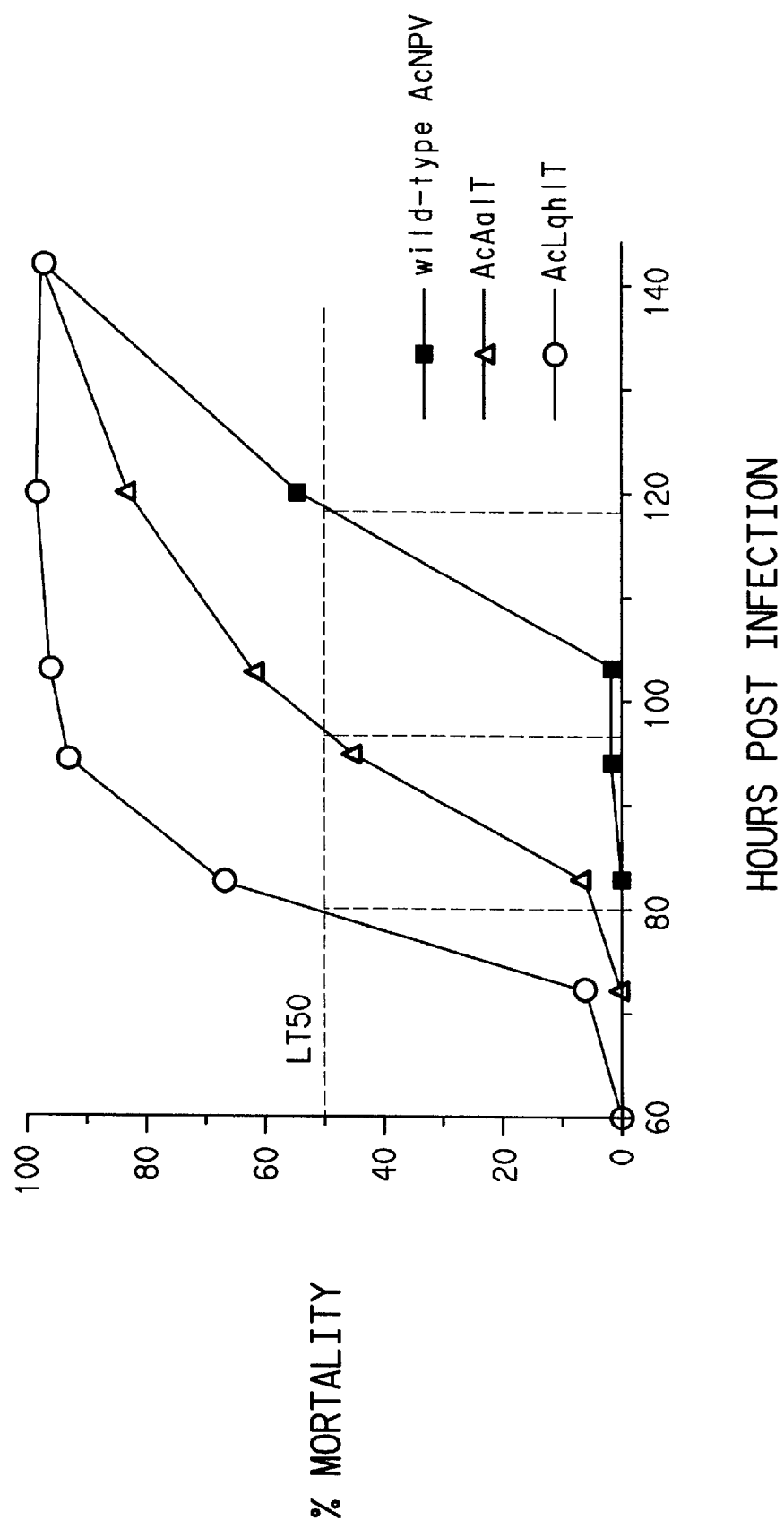

FIG. 6. Graphic representation of the time to mortality (Lethal Time) of 3rd instar larvae of *H. virescens* treated with AcLqhIT2 and control viruses.

FIG. 7. Graphic representation of inhibition of plant destruction (i.e., plant protection) by larvae of *H. virescens* treated with wild-type and recombinant baculoviruses. Data are reported as percent of leaf material remaining relative to control (uninfested) plants.

The present invention further comprises recombinant baculoviruses that have been deposited under the terms of the Budapest Treaty at American Type Culture Collection (ATCC), 12301 Parklawn Drive, Rockville, Md. 20852, and bear the following accession numbers:

| Recombinant Baculovirus | Accession Number | Date of Deposit |
| --- | --- | --- |
| AcLqhIT2 | ATCC VR-2501 | May 2, 1995 |
| CG201-3-1 | ATCC VR-2502 | May 2, 1995 |

Applicant has provided 14 sequence listings in conformity with "Rules for the Standard Representation of Nucleotide and Amino Acid sequences in Patent Applications" (Annexes I and II to the Decision of the President of the EPO, published in Supplement No. 2 to OJ EPO, 12/1992) and with 37 C.F.R. 1.821–1.825 and Appendices A and B ("Requirements for Application Disclosures Containing Nucleotides and/or Amino Acid Sequences").

DETAILED DESCRIPTION OF THE INVENTION

In the context of the present disclosure, a number of terms and abbreviations shall be used. "NPV" stands for Nuclear Polyhedrosis Virus. "PIBs" are polyhedrin inclusion bodies. "AcNPV" stands for the wild-type *Autographa californica* Nuclear Polyhedrosis Virus. "LqhIT2" represents the insect-selective neurotoxin derived from *Leiurus quinquestriatus hebraeus*. "AaIT" represents the insect-selective neurotoxin derived from *Androctonus australis*. "AcLqhIT2" is a short-hand form representing AcNPV that has been genetically modified to contain the gene encoding LqhIT2 under the transcriptional control of the baculovirus late P10 promoter. "AcAaIT" is a short-hand form representing AcNPV that has been genetically modified to harbor the gene encoding AaIT.

"Expression" refers to the transcription and translation of a structural gene to yield the encoded protein. As will be appreciated by those skilled in the art, structural gene expression levels are affected by the regulatory sequences (promoter, polyadenylation sites, enhancers, etc.) employed and by the host cell in which the structural gene is expressed.

As used herein, suitable "regulatory sequences" refer to nucleotide sequences located upstream (5'), within, and/or downstream (3') to a structural gene, which control the transcription and/or expression of the coding sequences, potentially in conjunction with the protein biosynthetic apparatus of the cell. These regulatory sequences include promoters, enhancer elements, transcription termination sequences, and polyadenylation sequences.

"Promoter" refers to the nucleotide sequences at the 5' end of a structural gene which direct the initiation of transcription. Promoter sequences are necessary, but not always sufficient, to drive the expression of a downstream gene. Usually promoters drive transcription preferentially in the downstream direction, although promotional activity can be demonstrated (at a reduced level of expression) when the gene is placed upstream of the promoter. The level of transcription is regulated by promoter sequences. Thus, in the construction of heterologous promoter/structural gene combinations, the structural gene is placed under the regulatory control of a promoter such that the expression of the gene is controlled by promoter sequences. The promoter is positioned preferentially upstream to the structural gene and at a distance from the transcription start site that approximates the distance between the promoter and the gene it controls in its natural setting. As is known in the art, some variation in this distance can be tolerated without loss of promoter function.

The "3' non-coding sequences" refers to the portion of the DNA sequence of a gene that contains a polyadenylation signal and any other regulatory signal capable of affecting mRNA processing or gene expression. The polyadenylation signal is usually characterized by affecting the addition of polyadenylic acid tracts to the 3' end of the mRNA precursor.

As used herein, "gene" refers to the entire DNA sequence portion involved in the synthesis of a protein. A gene embodies the structural or coding portion of DNA which begins at the 5' end from the translational start codon (usually ATG) and extends to the stop (TAG, TGA or TAA) codon at the 3' end. It also contains a promoter region, usually located 5' or upstream to the structural gene, which initiates and regulates the expression of a structural gene. Also included in a gene are the 3' non-coding sequences. "Chimeric gene" refers to a gene comprising heterogeneous regulatory and coding sequences. A "heterologous gene" refers to a gene not normally found in the host organism but that is introduced by gene transfer.

"Structural gene" is that portion of a gene comprising a DNA segment encoding a protein, polypeptide or a portion thereof, and excluding the 5' and 3' sequences involved in regulatory control of gene expression. The structural gene may be one which is normally found in the cell or one which is not normally found in the cellular location wherein it is introduced, in which case it is termed a heterologous gene. A heterologous gene may be derived in whole or in part from any source known to the art, including a bacterial genome or episome, eukaryotic, nuclear or plasmid DNA, cDNA, viral DNA or chemically synthesized DNA. A structural gene may contain one or more modifications in either the coding or the untranslated regions which could affect the biological activity or the chemical structure of the expression product, the rate of expression or the manner of expression control. Such modifications include, but are not limited to, mutations, insertions, deletions and substitutions of one or more nucleotides. The structural gene may constitute an uninterrupted coding sequence or it may include one or more introns, bounded by the appropriate splice junctions. The structural gene may be a composite of segments derived from a plurality of sources, naturally occurring or synthetic. The structural gene may also encode a fusion protein.

"Synthetic gene" refers to a DNA sequence of a structural gene that is chemically synthesized in its entirety or for the greater part of the coding region. As exemplified herein, oligonucleotide building blocks are synthesized using procedures known to those skilled in the art and are ligated and annealed to form gene segments which are then enzymatically assembled to construct the entire gene. As is recognized by those skilled in the art, functionally and structurally equivalent genes to the synthetic genes described herein may be prepared by site-specific mutagenesis or other related methods used in the art.

The term "operably linked" refers to nucleic acid sequences on a single nucleic acid molecule which are associated so that the function of one is affected by the other. For example, a promoter is operably linked with a structure gene when it is capable of affecting the expression of that structural gene (i.e., that the structural gene is under the transcriptional control of the promoter).

"Transfection" refers to stably introducing a DNA segment carrying a functional gene into an organism that did not previously contain that gene. "Co-transfection" refers to simultaneous introduction of more than one DNA segment into an organism.

"Codon-bias" refers to the preference exhibited by a specific host cell in usage of nucleotide codons to specify a given amino acid. When synthesizing a gene for improved expression in a host cell it is desirable to design the gene such that its frequency of codon usage approaches the frequency of preferred codon usage of the host cell. "Non-codon-biases" refers to unbiased, natural, native or wild-type.

"Chemically synthesized", as related to a sequence of DNA, means that the component nucleotides were assembled in vitro. Manual chemical synthesis of DNA may be accomplished using well established procedures (21), or automated chemical synthesis can be performed using one of a number of commercially available machines.

The present invention concerns construction and utilization of recombinant baculovirus insecticides, engineered to express the insect-selective neurotoxins. Disclosed is a synthetic gene encoding the authentic LqhIT2 toxin wherein codon usage has been biased towards codons frequently employed in highly expressed baculovirus genes in lepidopteran insects. Although the DNA sequence of this synthetic gene differs from the native LqhIT2 coding sequence, the encoded amino acid sequence is identical to the native toxin amino acid sequence. A chimeric gene comprising a baculovirus promoter, a nucleotide fragment encoding a signal peptide facilitating secretion of the expressed toxin, and the synthetic nucleic acid fragment encoding the toxin, was inserted into the genome of a nuclear polyhedrosis virus. Expression of this chimeric gene resulted in efficient toxin expression and enhancement of the insecticidal properties of the recombinant virus relative to non-recombinant baculoviruses. This improved activity is manifested by more rapid control of the target insect population and results in a significant reduction in feeding damage to crops caused by these insects. Surprisingly, the instant recombinant baculoviruses also displayed more rapid insect control than recombinant baculoviruses engineered to express another insect-selective toxin, AaIT.

Baculovirus insecticides have great potential to provide an environmentally benign method for agricultural insect pest control. However, improvements to efficacy are required in order to make these agents competitive with current chemical pest control agents. One approach for making such improvements is through genetic alteration of the virus. For instance, it may be possible to modify the viral genome in order to improve the host range of the virus, to increase the environmental stability and persistence of the virus or to improve the infectivity and transmission of the virus. In addition, improving the rate at which the virus acts to compromise the infected insect would significantly enhance the attractiveness of baculovirus insecticides as adjuncts or replacements for chemical pest control agents. One method for increasing the speed with which the virus affects its insect host is to introduce foreign genes that encode proteins that are toxic to the insect wherein death or incapacitation of the insect is no longer dependent solely on the course of the viral infection, but instead is aided by the accumulation of toxic levels of the foreign protein.

Many arthropods produce a mixture of substances referred to as venom. These substances are synthesized in specialized glandular tissues, which, when directed by a stinging or piercing apparatus, are capable of paralyzing the ardiropod's prey. Slow moving or stationary arthropods have adapted a strategy to instantaneously paralyze their prey by utilizing neurotoxic components of the venom at very low concentrations. These components or neurotoxins interfere with the function of insect nervous tissues through efficient competition for certain receptor sites. Many of these neurotoxins are polypeptides; these have been divided into different classes based on their host specificity and mode of action (22). For example, neurotoxic peptides isolated from numerous species of scorpions have been divided into classes that affect arthropods and classes that affect mammals.

Several of the arthropod-specific toxins have been identified as insect-selective peptides. For example, the Buthinae scorpions express two types of insect-selective neurotoxins that contrast in their biological effects on target insects. In the blowfly, those classified as excitatory toxins cause immediate, fast and reversible contractive paralysis caused by the induction and repetitive firing of the terminal branches of the motor neurons (23–25). These toxins are single-chained polypeptides of approximately 70 amino acids, and are cross-linked by four disulfide bridges. The excitatory effect is attributed to increased sodium conductance, and a voltage-dependent slowing of the channel's closure, resulting in negative discharges in effected neurons. AaIT, a toxin produced from the venom of the scorpion *Androctonus australis* (26), was the first insect toxin isolated from these organisms that exhibited this excitatory action.

A second class of insect-selective neurotoxins are the depressant toxins, including BjIT2 (27), LqqIT2 (28) and LqhIT2 (19). These toxins are polypeptides of 60 to 65 amino acids which possess unique and similar primary amino acid sequences that are distinct from the excitatory toxins. These toxins induce a slow, progressive paralysis and complete relaxation of the musculature of the insect. This activity is the result of the blockage of evoked action potentials (28, 29), and is attributable to the suppression of the sodium channel conductance and depolarization of the axonal membrane.

The methods and strategies used for preparation of recombinant baculoviruses that express heterologous genes are well known in the art (6, 7, 30). These methods of gene expression have afforded economic preparation of mammalian proteins in a eukaryotic expression vector system, in many instances resulting in proteins that have achieved their proper tertiary conformation and formed the proper disulfide bridges necessary for activity.

One method for introduction of heterologous genes into the baculovirus genome is by homologous recombination between viral genomic DNA and a suitable "transfer vector" containing the heterologous gene of interest. These transfer vectors are generally plasmid DNAs that are capable of autonomous replication in bacterial hosts, affording facile genetic manipulation. Baculovirus transfer vectors also contain a genetic cassette comprising a region of the viral genome that has been modified to include the following features (listed in the 5' to 3' direction): 1) viral DNA comprising the 5' region of a non-essential genomic region; 2) a viral promoter; 3) one or more DNA sequences encoding restriction enzyme sites facilitating insertion of heterologous DNA sequences; 4) a transcriptional termination sequence; and 5) viral DNA comprising the 3' region of a non-essential genomic region. A heterologous gene of interest is inserted into the transfer vector at the restriction site downstream of the viral promoter. The resulting cassette comprises a chimeric gene wherein the heterologous gene is under the transcriptional control of the viral promoter and transcription termination sequences present on the transfer vector. Moreover, this chimeric gene is flanked by viral DNA sequences that facilitate homologous recombination at a non-essential region of the viral genome. Recombinant viruses are created by co-transfecting insect cells (capable of supporting viral replication) with viral genomic DNA and the recombinant transfer vector. Homologous recombination between the flanking viral DNA sequences present on the transfer vector and the homologous sequences on the viral genomic DNA takes place and results in insertion of the chimeric gene into a region of the viral genome that does not disrupt an essential viral function. This recombined genomic DNA is eventually packaged into an infectious recombinant virion.

In a preferred embodiment, the non-essential region of the viral genome that is present on the transfer vector comprises the region of the viral DNA responsible for polyhedrin production. Most preferred is a transfer vector that contains the entire polyhedrin gene between the flanking sequences that are involved in homologous recombination. Recombination with genomic DNA from viruses that are defective in polyhedrin production (due to a defect in the genomic copy of the polyhedrin gene) will result in restoration of the polyhedrin-positive phenotype. This strategy facilitates identification and selection of recombinant viruses.

In another embodiment, baculoviral genomic DNA can be directly modified by introduction of a unique restriction enzyme recognition sequence into a non-essential region of the viral genome. A chimeric gene comprising the heterologous gene to be expressed by the recombinant virus, operably linked to regulatory sequences capable of directing gene expression in baculovirus-infected insect cells, can be constructed and inserted directly into the viral genome at the unique restriction site. This strategy eliminates the need for construction of transfer vectors and reliance on homologous recombination for generation of recombinant viruses. This technology is described by Ernst et al. (31) and in WO94/28114 (32).

Recombinant baculovirus vectors suitable for delivery of genetically encoded insect-specific neurotoxins require optimal toxin gene expression for maximum efficacy. A number of strategies can be employed by the skilled artisan to design and prepare recombinant baculoviruses wherein toxin gene expression results in sufficient quantities of toxin produced at appropriate times during infection in a functional form, and is available for binding to target cells within the insect host.

One key to optimal gene expression is selection of an appropriate promoter element that directs transcription of the gene. Several baculovirus promoters have been described that mediate gene expression at various levels, and at different times during the viral life cycle. For instance, the polyhedrin promoter is a very strong baculovirus promoter that directs the production of the polyhedrin protein, the primary protein comprising the viral nucleocapsid. This gene is expressed late during the viral life cycle, and messenger RNA encoded by this gene can account for 20% or more of the total polyadenylated message in the infected cell. Other promoters can be chosen that are of similar strength and are expressed late in the virus life cycle, including the P10 and basic promoters. Moreover, baculoviral promoters have been described that are induced by transcription factors early during the viral life cycle (33–36), including the immediately-early promoters IE1 and IEN, the delayed-early promoter 39 K or one of the promoters found on the HindIII-K fragment of the genome of AcNPV (49). These promoters may provide an additional means for accelerating the pest control capabilities of baculoviral insecticides.

Secretion of the synthesized toxin from recombinant baculovirus-infected cells is a prerequisite for more rapid onset of insecticidal effects in infected insects relative to effects induced by non-recombinant viruses (16,18). Eukaryotic proteins destined for extracellular secretion from the cell often employ short signal peptides for directing proteins to the endoplasmic reticulum. The signal peptide is then cleaved by a signal peptidase on the lumenal side of the endoplasmic reticulum membrane, and the mature protein, in this case an insect toxin, is packaged for secretion from the cell. O'Reilly et al. (6) have demonstrated that signal sequences are functional in the baculovirus expression system. Appropriate signal sequences can be selected from the group consisting of the cuticle signal sequence from *Drosophila melanogaster*, the chorion signal sequence from *Bombyx mori*, the apolipophorin signal sequence from *Manduca sexta*, the sex specific signal sequence from *Bombyx mori*, the adipokinetic hormone signal sequence from *Manduca sexta*, the pBMHPC-12 signal sequence from *Bombyx mori*, the esterase-6 signal sequence from *Drosophila melanogaster* and the signal sequence from the viral ecdysone glucosyltransferase protein. In addition, many naturally occurring signal sequences present on heterologous eukaryotic proteins will function in baculovirus-infected insect cells to mediate extracellular secretion.

The sequence of nucleotides encoding the signal peptide and the toxin protein may also impact the quantity of toxin produced, and thereby influence the efficiency and speed with which the infected insect succumbs to treatment with engineered viruses. Deviations in the nucleotide sequence that comprise the codons encoding the amino acids of the growing toxin polypeptide chain allow for variations in the sequence coding for the gene (37). Since each codon consists of three nucleotides, and the nucleotides comprising DNA are restricted to four specific bases, there are 64 possible combinations of nucleotides, 61 of which encode amino acids (the remaining three codons encode signals ending translation). As a result, many amino acids are designated by more than one codon. For example, the amino acids alanine and proline are coded for by four triplets, serine and arginine by six, whereas tryptophan and methionine are coded by just one triplet. This degeneracy allows for DNA base composition to vary over a wide range without altering the amino acid sequence of the proteins encoded by the DNA. One hypothesis for the evolutionary development and maintenance of this degeneracy is that the flexibility that results from the ability of several codons to encode a single amino acid minimizes the potential deleterious effects of point mutations in the nucleotide sequence. Accordingly, not all point mutations will result in a codon that directs the incorporation of an unexpected amino acid and thus results in synthesis of a missense protein, or in the insertion of a translational termination codon, resulting in premature termination of translation and the production of a truncated protein.

Many organisms display a bias for use of particular codons to code for insertion of a particular amino acid in a growing peptide chain. Codon preference or codon bias, differences in codon usage between organisms, is afforded by degeneracy of the genetic code, and is well documented among many organisms (38–43). Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in baculovirus expression systems based on optimization of these translational factors. Synthetic genes can thus be constructed in order to take advantage of the codon bias displayed by the virus genome. The skilled artisan appreciates the likelihood of successful gene expression if codon usage is biased towards those codons favored by the virus or the cells in which the virus replicates. Determination of preferred codons can be based on an exhaustive survey of viral and insect genes where sequence information is available. However, this information is of questionable value where the sequence information is derived from insects that are only distantly evolutionarily related to the natural host for the virus. For example, the use of codons biased on the genome of *Drosophila melanogaster* for expression of heterologous genes in AcNPV is not rational since the last common ancestor of flies (e.g., Drosophila) and moths (e.g., Lepidoptera) dates back approximately 250 million years (44, 45). More useful and compelling information for basing codon selection in favor of gene expression in NPVs can be obtained by simply examining codon bias in genes from the natural hosts of the virus (i.e., lepidopteran insects) and genes encoding highly expressed viral proteins.

Promoters directing expression of polyhedrin and P10 proteins of NPVs are known to be very late and strong promoters, and are therefore routinely chosen for directing expression of heterologous genes in baculovirus expression systems. In fact, 27 to 48 h after infection of an insect host cell by AcNPV, approximately 20% of the total polyadenylated RNA in the insect cell is polyhedrin mRNA (46, 47). In turn, the polyhedrin mRNA is efficiently translated, leading to an abundance of polyhedrin protein. Due to promoter strength and importance of the polyhedrin protein in the NPV life cycle, there has been constructed a synthetic version of the LqhIT2 gene based on the codon frequencies found in the NPV polyhedrin genes, including those from AcNPV, *Bombyx mori* NPV, *Spodoptera frugiperda* NPV, *Spodoptera littoralis* NPV and *Orgyia pseudotsugata* NPV. Codons were selected based on the frequency of appearance in these five NPV genes.

Preferred codons are easily detected when codons encoding the 20 amino acids and stop signal comprising the polyhedrin proteins are surveyed. For example, in the case of the amino acid glycine, GGC is the codon predominantly used at a frequency of 60% compared to GCA and GGG at frequencies of 14 and 4%, respectively. Other prefered codons are easily identified including: aspartic acid, GAC (74%) versus GAT (26%); arginine, CGC (37%) or CGT (33%) versus CCG (1%) or CGA (1%); asparagine, AAC (86%) versus AAT (14%); isoleucine, ATC (69%) versus ATA (6%); threonine, ACC (53%) versus ACA (4%) or ACG (13%); cystine, TGC (73%) versus TGT (27%); tyrosine, TAC (81%) versus TAT (19%); phenylalanine, TTC (65%) versus TTT (35%); glutaniine, CAA (94%) versus CAG (6%); histidine, CAC (83%) versus CAT (17%); and proline, CCC (58%) versus CCA (10%). On the basis of these predominant and distinct discrepancies in codon usage, we designed and synthesized a synthetic gene for LqhIT2.

In fact, the differences in codon usage observed in the NPV polyhedrin genes are also shared by the host cells and organisms that the viruses infect. The following Lepidopteran genes were considered:

| Insect | Gene | Accession No.[1] |
|---|---|---|
| Heliothis virescens | Cytochrome P-450 | U23506 |
| Heliothis virescens | Juvenile Hormone Binding Protein | U22515 |
| Heliothis virescens | Odorant Binding Protein | S62226 |
| Heliothis virescens | Pheromone Binding Protein | S62222 |
| Heliothis virescens | Mitochondrial p63 Chaperonin | X56034 |
| Heliothis virescens | ATPase | L16884 |
| Heliothis virescens | Juvenile Hormnone Esterase | J04955 |
| Trichoplusia ni | Preproattacin A | U46130 |
| Trichoplusia ni | Lysozyme Precursor Protein | U38782 |
| Trichoplusia ni | Cecropin A Precursor Protein | U38645 |
| Trichoplusia ni | HSP70 | U23504 |
| Trichoplusia ni | Basic Juvenile Hormone[8] Hemolymph Protein 2 | L03281 |
| Trichoplusia ni | Basic Juvenile Hormone[8] Hemolymph Protein 1 | L03280 |
| Spodoptera frugiperda | Endoprotease FURIN. | Z68888 |
| Spodoptera frugiperda | Immunophilin FKBP46 | U15038 |

[1]GenBank

In many instances, a similar codon preference was detected between the polyhedrin genes and lepidopteran genes. For example, in the case of aspartic acid, the codon GAC is used with 74% and 64% frequency for polyhedrin (polh) and lepidopteran (lep) genes, respectively. Other preferred codon frequencies include: isoleucine, ATC-polh 69% and ATC-lep 52%; threonine, ACC-polh 53% and ACC-lep 36%; cystine, TGC-polh 73% and TGC-lep 57%; tyrosine, TAC-polh 81% and TAC-lep 73%; and phenylalanine, TTC-polh 65% and TTC-lep 73%. In addition to this observable parallelism, in no case, in the comparison of polyhedrin and lepidopteran codon frequencies, does the use of a particular codon distinctly contrast between the two gene groups. Table 1 summarizes the frequency of codon utilization deduced from observation of five polyhedrin genes of nuclear polyhedrosis viruses and fifteen lepidopteran genes.

TABLE 1

Frequency of Codon Utilization in NPV Polyhedrin Genes and Lepidopteran genes

| Amino Acid | Codon | Frequency[1] Polyhedrin | Lepidopteran |
|---|---|---|---|
| Alanine | GCA | 0.08 | 0.19 |
| | GCC | 0.38 | 0.32 |
| | GCG | 0.25 | 0.20 |
| | GCT | 0.30 | 0.29 |
| Arginine | AGA | 0.12 | 0.17 |
| | AGG | 0.15 | 0.23 |
| | CGA | 0.01 | 0.09 |
| | CGC | 0.37 | 0.26 |
| | CGG | 0.01 | 0.08 |
| | CGT | 0.33 | 0.16 |
| Asparagine | AAC | 0.86 | 0.66 |
| | AAT | 0.14 | 0.34 |
| Aspartic Acid | GAC | 0.74 | 0.64 |
| | GAT | 0.26 | 0.36 |
| Cysteine | TGC | 0.73 | 0.57 |
| | TGT | 0.27 | 0.43 |
| Glutamine | CAA | 0.94 | 0.51 |
| | CAG | 0.06 | 0.49 |
| Glutamic Acid | GAA | 0.46 | 0.51 |
| | GAG | 0.54 | 0.49 |
| Glycine | GGA | 0.14 | 0.29 |
| | GGC | 0.60 | 0.26 |
| | GGG | 0.04 | 0.09 |
| | GGT | 0.23 | 0.35 |
| Histidine | CAC | 0.83 | 0.66 |
| | CAT | 0.17 | 0.34 |
| Isoleucine | ATA | 0.06 | 0.17 |
| | ATC | 0.69 | 0.52 |
| | ATT | 0.25 | 0.31 |
| Leucine | CTA | 0.13 | 0.09 |
| | CTC | 0.28 | 0.18 |
| | CTG | 0.27 | 0.27 |
| | CTT | 0.14 | 0.16 |
| | TTA | 0.07 | 0.12 |
| | TTG | 0.11 | 0.17 |
| Lysine | AAA | 0.46 | 0.36 |
| | AAG | 0.54 | 0.64 |
| Methionine | ATG | 1.00 | 1.00 |
| Phenylalanine | TTC | 0.65 | 0.73 |
| | TTT | 0.35 | 0.27 |
| Proline | CCA | 0.10 | 0.26 |
| | CCC | 0.58 | 0.26 |
| | CCG | 0.16 | 0.18 |
| | CCT | 0.15 | 0.30 |
| Serine | AGC | 0.29 | 0.15 |
| | AGT | 0.14 | 0.13 |
| | TCA | 0.06 | 0.17 |
| | TCC | 0.08 | 0.21 |
| | TCG | 0.29 | 0.14 |
| | TCT | 0.14 | 0.20 |
| Threonine | ACA | 0.04 | 0.23 |
| | ACC | 0.53 | 0.36 |
| | ACG | 0.13 | 0.14 |
| | ACT | 0.30 | 0.27 |
| Tryptophan | TGG | 1.00 | 1.00 |
| Tyrosine | TAC | 0.81 | 0.73 |
| | TAT | 0.19 | 0.27 |
| Valine | GTA | 0.12 | 0.23 |
| | GTC | 0.28 | 0.30 |
| | GTG | 0.43 | 0.24 |
| | GTT | 0.16 | 0.23 |
| End | TAA | 1.00 | 0.48 |
| | TAG | 0.00 | 0.33 |
| | TGA | 0.00 | 0.19 |

[1]A frequency value of 1.00 = 100%.

In some cases, alternative codons were chosen in order to facilitate genetic manipulation. The codon-biased version of the gene encoding the LqhIT2 toxin (SEQ ID NO:12) resulted in conversion of 41 of 186 nucleotides from those present in the cDNA copy of the native coding region of LqhIT2 (SEQ ID NO:11).

In order to prepare the codon-optimized LqhIT2 gene for insertion into a baculovirus vector, five sets of complimentary oligonucleotides (FIG. 2; SEQ ID NO:1–10) were designed and synthesized by standard synthetic methods, each encoding a specific region of the toxin protein. Each set of oligonucleotides, when annealed, formed a double stranded nucleic acid fragment possessing unique, single stranded extensions. The extensions were designed such that, upon incubation under appropriate conditions in the presence of a ligating enzymes, the fragments joined together in a directed, non-random fashion and resulted in a single nucleic acid fragment encoding a signal polypeptide linked to the authentic LqhIT2 toxin polypeptide. In addition, the resulting 5' and 3' ends encoded a restriction enzyme recognition site that, upon digestion with the appropriate enzyme, resulted in a DNA fragment that could be easily inserted into the insertion site of a previously prepared cloning vector. Ligated fragments were amplified by polymerase chain reaction, the amplified DNA was isolated and digested with an appropriate restriction enzyme, and the digested fragment was cloned into an intermediate plasmid vector. This intermediate vector facilitated manipulation and sequencing of the inserted toxin gene, thus facilitating confirmation of the identity of the inserted fragment, and to prepare for subsequent subcloning into an appropriate baculoviral transfer vector.

The confirmed toxin-encoding fragment was excised from the intermediate cloning vector and subcloned into a baculovirus transfer vector by standard molecular cloning techniques. In one embodiment, insertion into the transfer vector occurred at a position downstream of the baculoviral strong and late P10 promoter. This P10-LqhIT2 chimeric gene was flanked at the 5' and 3' ends by DNA sequences homologous to the regions of the baculovirus genome encoding the endogenous polyhedrin gene. Upon transformation of a suitable bacterial host, transformants were screened for proper orientation of the inserted fragments by observation of the electrophoretic migration of DNA following digestion with restriction endonucleases that cut the inserted DNA asymmetrically. A clone containing the insert in the correct orientation was chosen, and plasmid DNA of this recombinant transfer vector was prepared. In another embodiment, the synthetic LqhIT2 toxin-encoding structural gene was inserted into a baculovirus transfer vector at a position downstream of early IE1 promoter and hr5 enhancer regions. Identification of appropriate genetic constructs wherein the toxin structural gene was inserted into the early promoter transfer vector in the correct orientation relative to the promoter and enhancer element was carried out as described for the P10-LqhIT2 transfer vectors.

Introduction of the synthetic LqhIT2 gene into the baculovirus genome was accomplished by co-transfection of the transfer vector containing, inter alia, the chimeric signal peptide-toxin gene under the transcriptional control of either the P10 or IE1 promoters, the polyhedrin gene under the transcriptional control of the polyhedrin promoter, and flanking baculovirus DNA, and purified, linearized genomic DNA from a polyhedrin-negative baculovirus. These DNAs were introduced into transfection-competent insect cells by techniques well known in the art. Monolayers of transfected cells were observed for plaque formation, and plaques were observed for the presence of polyhedrin inclusion bodies. The presence of inclusion bodies indicated successful recombination of the region of the transfer vector containing the polyhedrin gene and the chimeric gene encoding LqhIT2 with the polyhedrin negative baculovirus DNA. The presence of the polyhedrin gene on the transfer vector compliments the lack of a functional polyhedrin gene on the baculovirus DNA, resulting in a facile method for screening for recombinant virus.

Insertion of the LqhIT2 gene into the baculovirus genome, resulting in recombinant baculoviruses, was confirmed by Western analysis with rabbit polyclonal antibodies specific for LqhIT2 toxin. Infected cell extracts were fractionated by SDS-PAGE and subsequently transferred to a suitable medium for detection by immunoblot analysis. Surprisingly, and in contrast to data reported by others, the infected cell extracts contained a polypeptide of molecular weight similar to that expected LqhIT2 that was specifically recognized by antibodies raised against purified LqhIT2 toxin. This is the first report of successful expression of a gene encoding the LqhIT2 protein.

Recombinant baculoviruses expressing LqhIT2 were evaluated for their ability to control a target insect population by measuring survival of first or third instar larvae of *H.* *virescens* after oral infection with the recombinant and wild-type AcNPV. Insect larvae were fed on diet inoculated with recombinant virus expressing the LqhIT2 toxin. In addition, control insects were allowed to feed on uninoculated diet or diet containing 1) wild-type, non-recombinant virus or 2) recombinant viruses expressing AaIT, a widely employed insect-specific scorpion toxin. Larvae were monitored for behavioral changes and, ultimately, mortality. Insects feeding on diet containing AcLqhIT2 or CG201-3-1 succumbed more rapidly than those fed wild-type virus. Surprisingly, recombinant viruses expressing LqhIT2 under the transcriptional control of either the late P10 promoter or the early IE1 promoter demonstrated more rapid insecticidal effects than recombinants expressing AaIT. Insect control efficacy of AcLqhIT2 was also demonstrated in plant protection experiments. Insect larvae were inoculated with test and control viruses by feeding on diet incorporating the various viruses. Infected larvae were placed on soybean plants, and, following a suitable incubation period, destruction of plant material was quantified. Results of the experiments indicated that AcLqhIT2 treatment results in significantly less plant destruction relative to wild-type virus and recombinant viruses expressing AaIT.

Compositions of this invention will generally be used in formulation with an agriculturally suitable carrier comprising a liquid or solid diluent. Useful formulations include dusts, granules, baits, pellets, suspensions, emulsions, wettable powders, dry flowables and the like, consistent with the physical properties of the active ingredient and compatible with the virus, mode of application and environmental factors such as soil type, moisture and temperature. Sprayable formulations can be extended in suitable media and used at spray volumes from about one to several hundred liters per hectare. High strength compositions are primarily used as intermediates for further formulation. The formulations will typically contain effective amounts of active ingredient, diluent and surfactant within the following approximate ranges which add up 100 weight percent.

|  | Weight Percent | | |
| --- | --- | --- | --- |
|  | Active Ingredient | Diluent | Surfactant |
| Wettable Powders | 5–90 | 0–74 | 1–10 |
| Oil Suspensions, Emulsions, Solutions, (including Emulsifiable Concentrates) | 5–50 | 40–95 | 0–15 |
| Dusts | 1–25 | 70–99 | 0–5 |
| Granules, Baits and Pellets | 0.01 99 | 5–99.99 | 0–15 |
| High Strength Compositions | 90–99 | 0–10 | 0–2 |

Typical solid diluents are described in Watkins, et al., *Handbook of Insecticide Dust Diluents and Carriers*, 2nd Ed., Dorland Books, Caldwell, N.J. Typical liquid diluents and solvents are described in Marsden, *Solvents Guide*, 2nd Ed., Interscience, New York, (1950). *McCutcheon's Detergents and Emulsifiers Annual*, Allured Publ. Corp., Ridgewood, N.J., as well as Sisely and Wood, *Encyclopedia of Surface Active Agents*, Chemical Publ. Co., Inc., New York, (1964), list surfactants and recommended uses. All formulations can contain minor amounts of additives to reduce foam, caking, corrosion, undesired microbiological growth, and the like. Care must be taken to ensure that all ingredients of the composition are mutually compatible and do not contribute to loss of the virus infectivity.

Fine solid compositions are made by blending and, usually, grinding as in a hammer mill or fluid energy mill.

Water-dispersible granules can be produced by agglomerating a fine powder composition; see for example, Cross et al., *Pesticide Formulations*, Washington, D.C., (1988), pp 251–259. Suspensions are prepared by wet-milling; see, for example, U.S. Pat. No. 3,060,084. Granules and pellets can be made by spraying the active material upon preformed granular carriers or by agglomeration techniques. See Browning, "Agglomeration", *Chemical Engineering*, Dec. 4, 1967, pp 147–148, *Perry's Chemical Engineer's Handbook*, 4th Ed., McGraw-Hill, New York, (1963), pages 8–57 and following, and WO 91/13546.

For further information regarding the art of formulation, see U.S. Pat. No. 3,235,361, Col. 6, line 16 through Col. 7, line 19 and Examples 10–41; U.S. Pat. No. 3,309,192, Col. 5, line 43 through Col. 7, line 62 and Examples 8, 12, 15, 39, 41, 52, 53, 58, 132, 138 –140, 162–164, 166, 167 and 169–182; U.S. Pat. No. 2,891,855, Col. 3, line 66 through Col. 5, line 17 and Examples 1–4; Klingman, *Weed Control as a Science*, John Wiley and Sons, Inc., New York, (1961), pp 81–96; and Hance et al., *Weed Control Handbook*, 8th Ed., Blackwell Scientific Publications, Oxford, (1989).

In the following examples, all percentages are by weight and all formulations are prepared in conventional ways.

Example A

| Wettable Powder | |
|---|---|
| baculovirus | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0%. |

Example B

| Granule | |
|---|---|
| baculovirus | 10.0% |
| attapulgite granules (low volatile matter, 0.71/0.30 mm; U.S.S. No. 25–50 sieves) | 90.0%. |

Example C

| Extruded Pellet | |
|---|---|
| baculovirus | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |

The compositions of this invention exhibit activity against a wide spectrum of foliar-feeding, fruit-feeding, stem feeding and seed-feeding lepidopterous pests important in agriculture, forestry, greenhouse crops, ornamentals, nursery crops and fiber products. Those skilled in the art will appreciate that not all compositions are equally effective against all growth stages of all pests. Nevertheless, all of the compositions of this invention display activity against larvae of the Order Lepidoptera. Specifically, the compositions are active against fall armyworm (*Spodoptera frugiperda*), tobacco budworm (*Heliothis virescens*), corn earworn (*Helicoverpa zea*), American bollworm (*Heliothis armigera*), beet armyworm (*Spodoptera exigua*), diamondback moth (*Plutella xylostella*) and cabbage looper (*Trichoplusia ni*).

Compositions of this invention can also be mixed with one or more other insecticides, fungicides, acaricides, or other biologically active compounds to form a multicomponent pesticide giving an even broader spectrum of agricultural protection. Examples of other agricultural protectants with which the recombinant baculoviruses of this invention can be formulated are insecticides that are sodium channel agonists (i.e., pyrethroids), sodium channel blocking agents (i.e., pyrazolines), acetylcholinesterase inhibitors (i.e., organophosphates and carbamates), nicotinic acetylcholine binding agents, gabaergic binding agents, octapine agonists or antagonists (i.e., formamidines) and oxyphos uncouplers (i.e., pyrrole insecticides). Specific examples of insecticides that can be mixed with the recombinant baculoviruses of this invention are: avermectin B, monocrotophos, tetrachlorvinphos, malathion, parathionmethyl, diazinon, profenofos, sulprofos, triflumuron, diflubenzuron, methoprene, buprofezin, thiodicarb, acephate, azinphosmethyl, chlorpyrifos, dimethoate, fipronil, flufenprox, fonophos, isofenphos, methidathion, metha-midophos, phosmet, phospharmidon, phosalone, pirimicarb, phorate, terbufos, trichlorfon, methoxychlor, bifenthrin, biphenate, tefluthrin, fenpropathrin, fluvalinate, imidacloprid, metaldehyde and rotenone. In addition, fungicides such as carbendazim, thiuram, dodine, maneb, chloroneb, benomyl, cymoxanil, fenpropidine, fenpropimorph, triadirnefon, captan, thiophanate-methyl, thiabendazole, phosethyl-Al , chlorothalonil, dichloran, metalaxyl, captafol, iprodione, oxadixyl, vinclozolin, kasugamycin, myclobutanil, tebuconazole, difenoconazole, diniconazole, fluquinconazole, ipconazole, metconazole, penconazole, propiconazole, uniconzole, flutriafol, prochloraz, pyrifenox, fenarimol, triadimenol, diclobutrazol, copper oxychloride, furalaxyl, folpet, flusilazol, blasticidin S, diclomezine, edifenphos, isoprothiolane, iprobenfos, mepronil, neo-asozin, pencycuron, probenazole, pyroquilon, tricyclazole, validamycin, and flutolanil can also be mixed with the recombinant baculoviruses of this invention.

In certain instances, combinations with other insecticides having a similar spectun of control but a different mode of action will be particularly advantageous for resistance management.

Lepidopterous pests are controlled and protection of agronomic, horticultural and specialty crops, animal and human health is achieved by applying one or more of the compositions of this invention, in an effective amount, to the environment of the pests including the agronomic and/or nonagronomic locus of infestation, to the area to be protected, or directly on the pests to be controlled. A preferred method of application is by spraying. Alternatively, granular formulations of these compounds can be applied to the plant foliage or the soil. Other methods of application include direct and residual sprays, aerial sprays, seed coats, microencapsulations, systemic uptake, foggers, aerosols, dusts and many others. The compositions can be incorporated into baits that are consumed by the insects or in devices such as traps and the like.

The compositions of this invention can be applied in their pure state, but most often application will be of a formulation comprising the instant baculoviruses with suitable carriers, diluents, and surfactants and possibly in combination with a food (bait) depending on the contemplated end use. A preferred method of application involves spraying a water dispersion or refined oil suspension of the arthropodicides. Combinations with spray oils, spray oil concentrations, spreader stickers, adjuvants, solvents, and synergists often enhance arthropodicidal efficacy.

The rate of application required for effective control will depend on such factors as the species of insect to be controlled, the pest's life cycle, life stage, its size, location, time of year, host crop or animal, feeding behavior, mating behavior, ambient moisture, temperature, and the like. Under normal circumstances, application rates of about 0.01 to 0.05 kg of active ingredient per hectare are sufficient to control pests in agronomic ecosystems, but as little as 0.001 kg/hectare may be sufficient or as much as 1 kg hectare may be required. For nonagronomic applications, effective use rates will range from about 1.0 to 50 mg/square meter but as little as 0.1 mg/square meter may be sufficient or as much as 150 mg/square meter may be required.

EXAMPLE 1

Construction of the Synthetic LqhIT2 Structural Gene

In order to prepare the NPV-biased form of the LqhIT2 gene, ten oligonucleotides were designed (FIG. 2; SEQ ID NO:1–10) and synthesized by standard phosphoramadite chemistry. These oligonucleotides were phosphorylated using Gibco/BRL (Gaithersburg, Md.) kinase, annealed, and ligated using Gibco/BRL ligase following the scheme depicted in FIG. 3, and employing the manufacturer's recommended protocols. Ligated fragments were then amplified by employing the polymerase chain reaction (PCR) using Perkin-Elmer Cetus AmpliTaq™ Polymerase (Norwalk, Conn.) according to the manufacturer's protocol and the modifications described below. Oligonucleotide Lq1 (SEQ ID NO:1) was used as the forward primer and oligonucleotide Lq10 (SEQ ID NO:10) served as the reverse primer. The descriptions of these protocols are set out below in greater detail.

Ten separate phosphorylation reactions (one for each oligonucleotide) were carried out. Two-hundred and fifty pmol of each oligonucleotide (SEQ ID NO:1–10) were placed in a 1.5 mL microcentrifuge tube. Five uL of 10× kinase buffer, 1 uL of 1 mM ATP, 6 uL of kinase (Gibco/BRL, 10 units/uL), and a sufficient volume of water was added to each tube in order to bring the total reaction volume to 50 uL. The ten tubes were incubated at 37° C. for 1 h. Following incubation, five uL of each phosphorylated oligonucleotide (25 pmol) was placed into a single microcentrifuge tube, and the tube was placed into a dry heat blockset at 95° C. The heat block was then turned off and allowed to cool to room temperature to facilitate annealing of phosphorylated oligonucleotides. Fifty uL of the mixture of phosphorylated, annealed oligonucleotides were placed into a separate microcentrifuge tube along with 15 uL of 5× ligase buffer, 3 uL of 10 mM ATP, 4 uL of ligase enzyme (Gibco/BRL, 5 units/uL) and 3 uL of deionized water. This tube was incubated at 37° C. for 30 min and subsequently stored at room temperature overnight.

The synthetic nucleic acid fragment comprising the annealed and ligated oligonucleotides was amplified by PCR. Three PCR reactions were performed on varying dilutions of template DNA (comprising the phosphorylated, annealed and ligated oligonucleotides). The following reaction mix was employed for PCR reactions:

61.5 uL of deionized water
10 uL of 10× PCR buffer (Perkin-Elmer Cetus)
2 uL each of DATP, dCTP, dGTP, dTTP (200 uM each)
0.5 uL of Ampli Taq™ Polymerase (2.5 units/100 uL)

Template DNA was diluted 1:100, 1:1,000 and 1:10,000 (v/v) with deionized water. Eighty uL of the reaction miix was placed in each of three 0.5 mL microcentrifuge tubes. Five uL (100 pmol) of oligonucleotide Lq1 (SEQ ID NO:1) and 5 uL (100 pmol) of oligonucleotide Lq10 (SEQ ID NO:10), (serving as the forward and reverse PCR primers) respectively, was added to each tube. Ten uL of appropriately diluted template was added to each tube. PCR reactions were carried out using a Perkin-Elmer DNA Thermocycler® programmed to carry out the following amplification protocol:

| STEP 1 | 96° C. | 3 minutes |
|---|---|---|
| 1 cycle | 75° C. | 3 minutes |
| STEP 2 | 95° C. | 30 seconds |
| 25 cycles | 75° C. | 2 minutes |
| STEP 3 | 95° C. | 30 seconds |
| 1 cycle | 75° C. | 5 minutes |

Products resulting from amplification were analyzed by electrophoresis through a 2% agarose gel. An amplified fragment of approximately 300 base pairs was observed for each reaction.

Following PCR amplification of the LqhIT2 gene and flanking regions, the 300 bp band was isolated from a 1.2% agarose gel and purified using a SpinBind DNA recovery system (FMC, Rockland, Me.) according to the manufacturer's protocol. The isolated fragment was digested with BamHI in order create cohesive 5' and 3' ends of the synthetic oligonucleotide containing the LqhIT2 gene and signal sequence. The digested fragment was then inserted into the pTZ-18R plasmid (Pharmacia, Piscataway, N.J.) at the BamHI cloning site using standard molecular cloning techniques. Following transformation of pTZ-18R into *E. coli* XL1 Blue (Stratagene, Menasha, Wis.), isolated colonies were chosen and plasmid DNA was prepared. Eight positive clones were identified and sequenced with the commercially available forward and reverse primers of PTZ-18R (Pharmacia). One clone (No. 16) was found to contain the correct sequence encoding for synthetic gene and signal sequence. The resulting plasmid contained two BamHI restriction sites: one site near the 5' end of the toxin gene and the other site following the stop codon. Plasmid DNA was prepared according to standard protocols, and was digested with BamHI to release the inserted 300 base pair fragment containing the LqhIT2 gene and signal sequence. This fragment was separated from vector sequences by electrophoresis through a 1.6% agarose gel, excision of the band corresponding to this fragment and purification by the SpinBind™ DNA recovery method (FMC).

EXAMPLE 2

Construction and Testing of Recombinant AcNPV Comprising the Synthetic LqhIT2 Structural Gene Under the Transcriptional Control of a Baculovirus Late Promoter The purified LqhIT2 gene fragment was inserted into the BglII cloning site of the baculovirus transfer vector pAcUW21 (Pharmingen, San Diego, Calif.) by standard molecular cloning techniques. This subcloning resulted in insertion of the synthetic gene on the 3' side of the vector-bome P10 promoter, and on the 5' side of a non-functional lacZ fragment resident on the transfer vector. Following ligation, DNA was transformed into the *E. coli* XL1 Blue (Stratagene). As a result of the ligation, both the BglII and BamHI sites were destroyed, and resulting plasmids were screened for a unique asymmetric SphI site located at the 3' end of the LqhIT2 gene. Three positive clones were identified from electrophoretic analysis of plasmid DNA isolated from twenty-three transformants. The direction of insertion was confirmed by analysis of plasmid digested simultaneously with SphI (cuts at the 3' end of the LqhIT2 gene) and BamHI (cuts within the coding sequence of the polyhedrin gene present on the transfer vector). One clone was identified as carrying the LqhIT2 gene in the correct orientation. This construction resulted in the LqhIT2 synthetic structural gene inserted downstream of the P10 promoter and upstream of the polyhedrin gene (pAcUW21.LqhIT2; see FIG. 5).

*Spodoptera frugiperda* cells (Sf-9) were propagated in "EXCELL" 401 media (JRH Biosciences, Lenexa, Kans.) supplemented with 3.0% fetal bovine serum. Lipofectin™ (50 µL at 0.1 mg/mL, Gibco/BRL) was added to a 50 µL aliquot of pAcUW21.LqhIT2 (500 ng) and linearized polyhedrin-negative AcNPV (2.5 µg, Baculogold™ viral DNA, Pharmingen). Sf-9 cells (approximate 50% monolayer) were co-transfected with the viral DNA/transfer vector solution. The supernatant fluid from the co-transfection experiment was collected at 5 days post-transfection and recombinant viruses were isolated employing standard plaque purification protocols, wherein only polyhedrin-positive plaques were selected (12).

A total of seven plaques were isolated; each was suspended in 500 µL of ExCell™ media supplemented with 2.5% fetal bovine serum. Sf-9 cells in 35 mM petri dishes (50% monolayer) were inoculated with 100 µL of the viral suspension, and supernatant fluids were collected at 5 days post infection. In order to prepare larger quantities of virus for characterization, these supernatant fluids were used to inoculate larger tissue cultures for large scale propagation of recombinant viruses.

Insertion of the LqhIT2 gene into the baculovirus genome was confirmed by immunoblot analysis and bioassay. Sf-9 cells (50 mL) were infected with wild-type AcNPV (control) or AcLqhIT2 (5 individual isolates). Three days post infection, infected cells were collected and growth media was removed by centrifugation of cell suspensions. Spent culture media was decanted and the remaining cells were lysed with a Branson Sonifier™ (Model 450) for 30 s at setting 2. Cellular debris was then removed by centrifugation at 15,000 rpm for 10 min in a refrigerated microcentrifuge (4° C.).

Protein concentrations of cell infected cell sonicates were quantified using the BCA Protein Assay (Pierce, Rockford, Ill.) according to the manufacturer's instructions. A standard curve was prepared based on known concentrations of Bovine Serum Albumin. Samples and standards were incubated for 30 min at 37° C., and the absorbence at 562 nm was measured with a spectrophotometer. Protein concentrations were determined for each sample by linear regression analysis.

Individual proteins in quantified samples were separated by protein electrophoresis. Samples were diluted to 3–4 mg/mL protein with deionized water. Twenty-five µL of each sample was added to 75 µL of electrophoresis sample buffer (3.8 mL deionized $H_2O$, 1.0 mL 0.5 M Tris-HCl, pH 6.8, 0.8 mL glycerol, 1.6 mL 10% (w/v) SDS, 0.4 mL β-mercaptoethanol, 0.4 mL 0.5% bromophenol blue). Molecular weight standards were prepared by diluting 1 µl of biotinylated protein molecular weight standards (Gibco) in 100 µL of sample buffer. Samples and standards were then heated at 95° C. for 2 min. Samples were loaded (20 µl/well) onto a 15% Mini-Protean II Tris-HCl Ready Gel (Bio-Rad, Melville, N.Y.). Electrophoresis running buffer (3 g Tris base, 14.4 g glycine, 1.0 g SDS in 1 L deionized $H_2O$) was added to the assembled electrophoresis gel apparatus and samples were electrophoresised for approximately 1.5 h at 40 mA.

Following electrophoresis, separated proteins were transferred from the electrophoretic gel to a nitrocellulose filter by western blotting. Blotter paper (3MM; Schleicher and Schuell, Keene, N.H.) and nitrocellulose (BA-S NC; Schleicher and Schuell) were cut to the approximate dimensions of the gel and soaked in western transfer buffer (11.6 g Tris base, pH 8.3, 5.8 g glycine, 0.74 g SDS, 400 mL methanol, 1.6 L deionized $H_2O$). The blotter paper, nitrocellulose and gel were assembled in the following sequence: 3 sheets of blotter paper, gel, nitrocellulose, and 3 pieces of blotter paper. This "sandwich" was placed in the transfer apparatus such that the gel was oriented towards the cathode and the nitrocellulose membrane towards the anode. Proteins were transferred by applying a current to the transfer apparatus for 4 h at 60 mA. Following transfer, the apparatus was disassembled and the nitrocellulose filter was allowed to air dry.

Immunoblot analysis of transferred proteins proceeded by the following steps, all of which were performed on a rotary shaker at room temperature. Sites on the nitrocellulose membrane that were unoccupied by transferred proteins were blocked with 3% (w/v) gelatin dissolved in TTBS (20 mM Tris, 500 mM NaCl, pH 7.5, 0.05% Tween-20) by incubation for 30 min. The blocking solution was removed and the membrane was rinsed in 100 mL TTBS for 5 min. LqhIT2-specific rabbit polyclonal antibody (obtained from Dr. Bruce Hammock, U.C. Davis, Davis, Calif.) was prepared by adding 10 µL rabbit antibody to 10 mL TTBS. This primary antibody solution was applied to the blocked nitrocellulose filter and incubated for 1 h. Following this incubation, the nitrocellulose filter was washed in 3 changes of 100 mL TTBS, each wash lasting 10 min. The secondary antibody was prepared by adding 10 µL peroxidase conjugated goat antirabbit IgG (Sigma, St. Louis, Mo.) and 10 µL peroxidase-labeled streptavidin to 20 mL TTBS. The nitrocellulose filter was incubated with this solution for 1 h. Following this incubation, the filter was washed in 3 changes of 100 mL TTBS, each wash lasting 10 min. Detection reagent (ECL Detection kit; Amersham, Arling Heights, Ill.) was applied to the nitrocellulose and incubated for 60 s. The detection reagent was drained from the filter, and the filter was covered with Saran Wrap. Signal from the nitrocellulose filter was detected by exposing the processed membrane to X-ray film (Kodak X-OMAT AR, Rochester, N.Y.) for 2–10 s. All five AcLqhIT2 isolates provided a positive inmmunoblot response near 7,000 Mr, whereas no signal was detected for AcAaIT.

Five independent AcLqhIT2 isolates were screened for biological activity. This assay involved comparison of biological activity of AcLqhIT2 recombinant viruses to wild-type AcNPV (control) and recombinant AcNPVs expressing the AaIT toxin. Third instar larvae of *H. virescens* were infected orally by consumption of diet that contained test and control viruses, and monitored for behavioral changes and mortality.

Cells infected with AcLqhIT2, AcNPV and AcAaIT were harvested, and PIBs were released by consecutive washes with 0.5% w/v sodium dodecyl sulfate, 5M NaCl, and finally deionized water. After the water wash, freed PIBs were suspended in a small volume of deionized water and enumerated by hemocytometer counting. It was noted that significantly less PIBs and cellular debris were produced from Sf-9 cells infected with AcLqhIT2 three to four days post infection than from cells infected with wild-type AcNPV and AcAaIT.

Isolated plugs of a standard insect diet were inoculated with approximately 5000 PIBs. Individual larvae that had not fed for 12 h prior to beginning of the bioassay were allowed to consume the diet for 24 h. The larvae were transferred to an individual well in a diet tray and monitored for symptoms and mortality on a daily basis. These initial bioassays demonstrated the induction of paralysis after consumption of diet containing AcLqhIT2 and AcAaIT viruses. Surprisingly, AcLqhIT2 appeared to kill larvae more rapidly than either wild-type AcNPV or AcAaIT viruses. Three of the AcLqhIT2 isolates tested and the best AcAaIT virus were chosen for subsequent testing. Once again, the results indicated that the AcLqhIT2 viruses resulted in more rapid mortality than either of the controls.

A thorough evaluation of the insecticidal effects of the recombinant viruses was undertaken. Earlier observations indicated that the expression of LqhIT2 by AcNPV produces a cytotoxic effect in insect cells. Moreover, due to this cytotoxic effect, the yield of PIBs/cell for AcLqhIT2 is significantly reduced in comparison to wild-type AcNPV and AcAaIT. In fact, cell cultures infected with AcLqhIT2 yielded average PIB counts of $5.03 \times 10^7$/100 mL of cell culture media compared to $>1.9 \times 10^9$ PIBs/100 mL of cell culture media for AcAaIT and wild-type AcNPV. In order to prepare even larger quantities of AcLqhIT2 recombinant PIBs, viruses were propagated in vivo. To acquire in vivo produced PIBs of AcLqhIT2, AcAaIT and wild-type AcNPV, the dead insects from preliminary bioassays were processed by homogenization in deionized water, followed by probe sonification and filtration to remove cellular debris. PIBs were then enumerated using a standard hemocytometer.

Comprehensive analysis of virus-induced insect mortality was performed in experiments wherein third instar larvae of *H. virescens* were infected with test and control viruses and observed for onset of mortality. A probit analysis program (48) was used to derive time-mortality and dose-mortality curves (Table 2), and to test for significant differences in bioactivity of the recombinant (AcLqhIT2 and AcAaIT) and wild-type AcNPVs. Lethal times (LTs) were derived by allowing starved insects to feed for 24 h on diet plugs that were inoculated with 2500 PIBs per plug. These insects were then transferred to individuals wells of diet and were routinely monitored (at least twice a day) for death and/or paralysis. The approximate $LT_{50}$ (time to kill 50% of the exposed insects; 8 replicates, 16 larvae per replicate, n=128 insects per treatment) for AcLqhIT2, AcAaIT and wild-type AcNPV were 82.7, 97.9 and 118 h post infection, respectively. The likelihood-ratio test (equal slopes and intercepts, C.I.=0.95) demonstrated a significant difference among treatments: recombinant viruses, AcLqhIT2 and AcAaIT, had significantly lower LT values than larvae infected with wild-type AcNPV. Furthermore, a direct comparison of slopes and intercepts (C.I.=0.95) of the AcLqhIT2 and AcAaIT recombinant viruses confirmed that the $LT_{50}$ values for AcLqhIT2 were significantly lower than those for AcAaIT.

In a second set of experiments, lethal doses (LDs) were determined. Third instar larvae of *H. virescens* were fed on diets inoculated with AcLqhIT2, AcAaIT, wild-type AcNPV, and uninoculated plugs. Molten diet was prepared with varying doses of virus in order to establish dose-response curves for the sample groups. PIB concentrations of the diet plugs ranged in logarithmic dose from $1 \times 10^2$ through $1 \times 10^4$ PIBs per mL of diet. The test was monitored for mortality between at 94 and 160 h post feeding. The approximate $LD_{50}$s (number of PIBs required to kill 50% of the exposed insects; 4 replicates, 25 larvae per replicate, n=100 insects per treatment) for AcLqhIT2, AcAaIT and wild-type AcNPV were $8.29 \times 10^2$, $9.15 \times 10^2$ and $1.19 \times 10^3$ PIB/mL, respectively. The likelihood-ratio test (equal slopes and intercepts, C.I.=0.95) showed no significant difference between the potency of the three viral treatments (Table 2).

TABLE 2

Lethal Doses and Times of Recombinant Viruses on 3rd Instar Larvae of *H. virescens*

| Virus | LD (PIBs × $10^2$/mL) | | | LT (hours) | | |
|---|---|---|---|---|---|---|
| | 10 | 50 | 90 | 10 | 50 | 90 |
| AcLqhIT2 | 1.03 | 8.29 | 66.6 | 66.8[a] | 82.7[a] | 102[a] |
| AcAaIT | 1.55 | 9.15 | 53.9 | 76.7[b] | 97.9[b] | 125[b] |
| Wild-type AcNPV | 2.52 | 11.9 | 56.1 | 95.6[c] | 118[c] | 145[c] |

[a, b, c] Significantly different from other treatments - POLO probit analysis program (C.I. 0.95).
PIBs = polyhedrin inclusion bodies.
LD = lethal dose.
LT = lethal time.

Further evaluation of efficacy of the viruses was conducted on two week-old soybean (Williams) plants potted in 4 inch square pots filled with METROMIX 350 growth medium (Grace-Sierra, Milpitas, Calif.). These plants were grown in a greenhouse at 26° C. Second instar larvae of *H. virescens* were exposed for 24 h to the viral treatments which were incorporated into the diet at a concentration calculated to result in fatal infection of greater than 99% of treated insects. Following this exposure period, infected insects were transferred to the plants. The plant set-up consisted of one soybean plant enclosed in a clear plastic-tube with an open top. A layer of white silica sand was placed on top of the potting media so fallen insects could be easily identified. Three treated insects were placed on the plant and the unit top was closed. Ten plants were used per treatment.

The test units were held in a plant holding room on a 16 h light and 8 h dark cycle and watered as needed. At the conclusion of the testing period (death of all treated insects) the test units were disassembled and plant material was quantified, employing a Li-Cor leaf area meter (Li-Cor, Lincoln, Nebr.). The average plant area remaining was 154, 199, 223 cm$^2$ for wild-type AcNPV, AcAaIT and AcLqhIT2, respectively, while untreated (controls) plants had an average of 243 cm$^2$ of material. These data indicate 63.6, 82.2 and 92.1 percent plant protection for wild-type AcNPV, AcAaIT and AcLqhIT2, respectively, when compared to uninfested plants (FIG. 7). Clearly, the recombinant viruses expressing the toxins provide increased protection, and the AcLqhIT2 provides significantly greater protection than AcAaIT.

EXAMPLE 3

Construction and Testing of Recombinant AcNPV Comprising the Synthetic LqhIT2 Structural Gene Under the Transcriptional Control of a Baculovirus Early Promoter In the same manner as described in Example 2, the purified LqhIT2 structural gene gene fragment from Example 1 was inserted into the BglII cloning site of the baculovirus transfer vector pAcP+IE1TV3 (provided by Dr. Donald Jarvis, Texas Agricultural Experiment Station, Texas A&M University, College Station, Tex.). This plasmid transfer vector is a derivative of the baculovirus early promoter transfer vectors described in U.S. Pat. No. 5,162,222, incorporated herein by reference. This construct resulted in the insertion of the synthetic structural gene encoding the LqhIT2 toxin downstream of the baculovirus early IE1 promoter and the hr5 enhancer region. Following ligation, plasmid DNA was transformed into the E. coli XL1 Blue (Stratagene). As a result of the ligation, both the BglII and BamHI sites were destroyed, and resultant transformants were screened for possession of plasmids that contained a unique asymmetric SphI site located at the 3' end of the LqhIT2 gene.

Twenty-three SphI-positive clones were identified from electrophoretic analysis of plasmid DNA isolated from twenty-four transformants. The direction of insertion was confirmed by analysis of plasmid digested simultaneously with SphI (cuts at the 3' end of the LqhIT2 gene) and StuI (cuts within the coding sequence of the multiple clonining site present in the transfer vector downstream of the BglII cloning site). Eight clones were analyzed, four of which possessed the LqhIT2 gene in the correct orientation relative to the direction of transcription from the early IE1 promoter/hr5 enhancer regions. DNA from one of the clones, CG201-3, was isolated and utilized to create recombinant baculovirus expression vectors by co-tratisfection, essentially following the protocol described in Example 2. Plaques were isolated and propagated in tissue culture, and insecticidal activity was determined by bioassay, following the protocols described in Example 2.

Neonate larvae of H. virescens were infected with test and control viruses and observed for the onset of mortality. For this set of bioassays, the virus was incorporated into the insect diet at a concentration of $1.0 \times 10^4$ PIBs/mL. A probit analysis program (48) was used to derive time-mortality curves and to test for signficant differences in bioactivty of the recombinant viruses (CG201-3-1 and AcLqhIT) and wild-type AcNPV. The approximate $LT_{50}$ (time to mortality for 50% of the treated insects) for CG201-3-1, AcLqhIT and wild-type AcNPV were 44.4, 61.5 and 91.0, respectively (4 replicates, 25 larvae per replicate, n=100 insects per treatment; Table 3). The likelihood ratio test (C.I.=0.95) demonstrated a significant difference among treatments, indicating that application of either of the recombinant viruses resulted in more rapid mortality than treatment with wild-type AcNPV. More specifically, CG201-3-1 had significantly lower LT values than AcLqhIT, indicating that this recombinant virus kills treated insects more rapidly. This data demonstrates that utilization of an early promoter to drive expression of a codon-biased, synthetic structural gene encoding an insect-specific toxin reduces the time to mortality by 27.8% compared to viruses where expression of an identical structural gene is controlled by a late promoter. Moreover, these data indicate that viruses expressing the synthetic toxin gene under the transcriptional control of an early promoter reduce the time to mortality of treated insect larvae by greater than 50% when compared to treatment with non-recombinant, wild-type AcNPV.

TABLE 3

Lethal Times of of Recombinant Viruses on 1st Instar Larvae of H. virescens

| Virus | LT (hours) | | |
|---|---|---|---|
| | 10 | 50 | 90 |
| CG201-3-1 | 32.7[a] | 44.4[a] | 60.3[a] |
| AcLqhIT | 47.4[b] | 61.5[b] | 79.6[b] |
| Wild-type AcNPV | 75.9[c] | 91.0[c] | 109[c] |

[a, b, c]Significantly different from other treatments - POLO probit analysis program (C.I. 0.95).
LT = lethal time.

EXAMPLE 4

Construction and Testing of a Recombinant AcNPV Comprising a Synthetic LqhIT2 Structural Gene Based on the Complimentary DNA of the LqhIT2 Gene Isolated from the Scorpion, Leiurus quinquestriatus hebraeus In order to evaluate increased efficacy provided by the NPV-codon biased LqhIT2 gene versus the cDNA version, the cDNA gene was synthesized and incorporated into the AcNPV viral genome by methods analogous to those described in Examples 1, 2 and 3.

The synthetic cDNA LqhIT2 gene was generated, isolated, subcloned and sequenced in a similar manner to the codon biased LqhIT2 gene described in Example 1. In order to prepare the cDNA form of the LqhIT2 gene, ten oligonucleotides were designed and synthesized by standard phosphoramadite chemistry. These oligonucleotides were phosphorylated using Gibco/BRL (Gaithersburg, Md.) kinase, annealed, and ligated using Gibco/BRL ligase following the scheme depicted in FIG. 3, and employing the manufacturer's recommended protocols. Ligated fragments were then amplified by polymerase chain reaction (PCR) using Perlin-Elmer Cetus AmpliTaq Polymerase (Norwalk, Conn.) according to the manufacturer's protocol and the modifications described below.

After PCR amplification, the gene product was cloned into the pCRTMII Vector according to the protocol provided in the Original TA Cloning Kit (Invitrogen, San Diego, Calif.). Following ligation, transformation and restriction map analysis, several clones were sequenced and a clone was confirmed to encode for the bombyxin signal sequence and the cDNA version of the LqhIT2 gene. The gene was inserted into the SacI/NotI cloning sites of the baculovirus transfer vector pAcP+IE1TV3. Recombinant AcNPVs were constructed using the protocols according to details described in Example 2.

Following the propogation of five candidate recombinant viruses encoding the cDNA LqhIT2 gene (IC735), the viruses were tested for efficacy, and the best viral isolate with respect to lethal time values was selected. Lethal time characterization was performed on neonate larvae, and third and fourth instar larvae of H. virescens for the codon optimized AcLqhIT2 (CG201-3-1), the cDNA version of AcLqhIT2 (IC735-1), and wild-type AcNPV (IC200-27) to determine any significant differences in time to kill (Table 4).

For third and fourth instar larvae, a diet pill assay was utilized to determine $LT_{50}$ values. Stock preparations of viruses were quantified using a Reichert-Jung bright-line hemacytometer. Viral suspensions were formulated in deionized water to a final concentration of 1000–2000 PIBs/uL. Individual 50 uL diet pills were placed in each well of a sixteen-well polystyrene bioassay tray. A dose of 5000 OBs was applied to the surface of each 50 uL diet pill, and the viral treatment was allowed to dry. One larva was then placed into each well; wells were sealed and incubated at 28° C. Upon complete consumption of the diet pill (approx. 24 hrs), the larvae were transferred to untreated insect media and evaluated for mortality twice daily.

For neonate larvae, a diet incorporation assay was utilized to determine $LT_{50}$ values. Stock virus preparations were quantified using a Reichert-Jung bright-line hemacytometer and diluted with deionized water to a concentration of $1.0 \times 10^5$ PIBs/mL. A final 1:10 dilution was performed in insect media. This virus-containing media was blended for 30 seconds to ensure a homogenous suspension of viral occlusion bodies at $1.0 \times 10^4$ PIBs/mL. The media was then poured into cells of polystyrene trays, each tray containing 25 cells. Approximately 2 mL of diet was applied to each cell. Upon solidification of the inoculated media, one neonate H. virescens larva was placed into each cell. Cells were sealed and incubated at 28° C. Evaluations for larval mortality were performed twice daily.

Data from these experiments was analyzed using the Vistat statistical analysis package (50). For all three larval stages tested, the CG201-3-1 encoding the codon-biased LqhIT2 gene killed insect larvae more rapidly than IC735-1 (the cDNA version of LqhIT2), and IC200-27 (wild-type AcNPV). The reduction in $LT_{50}$ values for the codon optimized CG201-3-1 compared to IC735-1 was statistically significant for third and fourth instar larvae of H. virescens, with a reduction in time to kill of 22% and 9%, respectively (Table 4). These differences were even more dramatic at the $LT_{90}$s for neonate and third instar larvae, with approximately 15% and 32% reduction in time to kill, respctively, with the codon optintized construct, CG201-3-1 (48).

TABLE 4

Lethal Times ($LT_{50}$) of Recombinant or Wild-type Viruses on Neonate and Selected Instars of Larvae of *H. virescens*

| | $LT_{50}$ (hours) | | |
|---|---|---|---|
| Virus | Neonate | Third Instar | Fourth Instar |
| CG201-3-1 | 61.7 | 62.9 | 69.3 |
| IC735-1 | 65.0 | 81.0 | 76.1 |
| Wild-type AcNPV | 102 | 113 | 111 |

References (1) Granados, R. R.; Lawler, K. A. *Virology* (1981), 108, 297–308.
(2) Vlak, J. M.; Rohrmann, G. F. In *Viral Insecticides for Biological Control*, Maramorosch, K.; Sherman, K. E., Eds.; Academic Press, New York, N.Y. (1985), 489–542.
(3) Carbonell, L. F.; Klowden, M. J; Miller, L. K. *J. Virol.* (1985), 56, 153–160.
(4) Carbonell, L. F.; Miller, L. K. *Appl. Environ. Microbiol.* (1987), 53, 1412–1417.
(5) Brusca, J.; Summners, M; Couch, J.; Courtney, L. *Intervirol.* (1986), 26, 207–222.
(6) O'Reilly, D. R.; Miller, L. K.; Luckow, V. A. (1992), *Baculovirus Expression Vectors: A Laboratory Manual*, W. H. Freeman and Company, New York.
(7) King, L. A.; Possee, R. D. (1992), *The Baculovirus Expression System*, Chapman and Hall, London.
(8) O'Reilly, D. R.; Miller, L. K. *J. Virol.* (1990), 64, 1321–1328.
(9) O'Reilly, D. R.; Miller, L. K. *Science* (1989), 245, 1110–1112.
(10) O'Reilly, D. R.; Miller, L. K., *Biotechnol.* (1991), 9, 1086–1089.
(11) Carbonell, L. F.; Hodge, M. R.; Tomalski, M. D.; Miller, L. K. *Gene* (1988), 73, 409–418.
(12) Merryweather, A. T.; Weyer, U.; Harris, M. P. G.; Hirst, M.; Booth, T.; and Possee, R. D. *J. Gen. Virol.* (1990), 71, 1535–1544.
(13) Martens, J. W. M.; Honee, G.; Zuidema, D.; Van Lent, J. W. M.; Visser, B; Vlak, J. M. *Appl. Environ. Microbiol.* (1990), 56, 2764–2770.
(14) Tomalski, M. D.; Miller, L. K. *Nature* (1991), 352, 82–85.
(15) Tomalski, M. D.; Miller, L. K. *Biotech.* (1992), 10, 545–549.
(16) Maeda, S.; Volrath, S. L.; Hanzlik, T. N.; Harper, S. A.; Maddox, D. W.; Hammock, B. D.; Fowler, E. *Virol.* (1991), 184, 777–780.
(17) Stewart, L. M. D.; Hirst, M.; Ferber, M. L.; Merryweather, A. T.; Cayley, P. J.; Possee, R. D. *Nature* (1991), 352, 85–88.
(18) McCutchen, B. F.; Choudary, P. V.; Crenshaw, R.; Maddox, D.; Kamita, S. G.; Palekar, N.; Volrath, S.; Fowler, E.; Hammock, B. D.; Maeda, S. *Biotech.* (1991), 9, 848–852.
(19) Zlotkin, E.; Eitan, M.; Bindokas, V. P.; Adams, M. E.; Moyer, M.; Burkhart, W.; Fowler, E. *Biochemistry* (1991), 30, 4814–4821.
(20) Zilberberg, N.; Zlotkin, E.; Gurevitz, M. *Insect biochem. Molec. Biol.* (1992), 22, 199 203.
(21) Caruthers, M., in *Methodology of DNA and RNA Sequencing*, (1983), Weissman (ed.), Praeger Publishers, New York, Chapter 1.
(22) Zlotkin, E. *Phytoparasitica* (1991). 19, 177–182.
(23) Walther, D.; Zlotkin, E.; Rathmayer, E. *J. Insect Physiol.* (1976), 22, 1187–1194.
(24) Zlotkin, E. in *Neuropharmacology and Pesticide Action*; (1986), Ford, Lunt, Raey & Usherwood (eds.), Ellis Horwood, England, 352–383.
(25) Zlotkin, E.; Fishman, L.; Gordon, D. in *Neurotox'88: Molecular Basis of Drug and Pesticide Action*, (1988), Lunt (ed.) 35–47.
(26) Zlotkin, E.; Rochat, H.; Kupeyan, C.; Miranda, F.; Lissitzky, *S. Biochimie* (Paris) (1971),53, 1073–1078.
(27) Lester, D.; Lazarovici, P.; Pelhate, M.; Zlotkin, E *Biochem. Biophys. Acta.* (1982), 701, 370–381.
(28) Zlotkin, E.; Kaduri, D.; Gordon, D.; Pelhate, M.; Martin, M.; Rochat, H. *Arch. Biochem. Biophys.* (1985), 240, 877–887.
(29) Zlotkin, E.; Gurevitz, M.; Fowler, E.; Adams, M. *Arch. of Insect Biochem. Physiol.* (1993), 22, 55–73.
(30) U.S. Pat. No. 4,745,051.
(31) Ernst, W.; Grabherr, R.; Katinger, H. *Nuc. Acid Res.* (1994), 22, 2855–2856.
(32) Patent Cooperation Treaty, Publication Number WO 94/28114.
(33) Jarvis, D.; Fleming, J.; Kovacs, G.; Sumirners, M.; Guarino, L. *Biotechnol.* (1990), 8, 950–955.
(34) O'Reilly, D.; Passarelli, L.; Goldman, I.; Miller, L. *J. Gen. Virol.* (1990), 71, 1029–1037.
(35) Guarino, L.; Summers, M.; *J. Virol.* (1987), 61, 2091–2099.
(36) Crawford, A.; Miller, L. *J. Virol.*, (1988), 62, 2773–2781.
(37) Alberts et al., *Molecular Biology of the Cell*, Garland, New York, pp 106–111.

(38) Grantham, R. et al. *Nucl. Acids Res.* (1980), 8, 49–62.
(39) Grantham, R. et al. *Nucl. Acids Res.* (1980), 9, 43–74.
(40) Aota, S. et al. *Nucl. Acids Res.* (1988), 16, 315–402.
(41) Maroyama, T. et al. *Nucl. Acids Res.* (1986), 14, 151–197.
(42) Wada, K. et al. *Nucl. Acids Res.* (1991), 19, 1981–1985.
(43) Kurland, C., *FEBS Letters*, (1991), 285, 165–169.
(44) Mitsialis, A.; Kafatos F. *Nature*, (1985), 317, 453–456.
(45) Merriam, J.; Ashbumer, M.; Hartl, D; Kafatos, F. *Science*, (1991), 254, 221–225.
(46) Adang, M.; Miller, L. *J. Virol.*, (1982), 44, 782–793.
(47) Rohel, D.; Cochran, M.; Faulkner, P. *Virology*, (1983), 124, 357–365.
(48) Leora Software, (1987). POLO-PC A user's guide to probit or logit analysis, Berkeley, Calif.
(49) U.S. Pat. No. 5,162,222
(50) Boyce Thompson Institute at Cornell University, Ithaca, N.Y. (Copyright 1990, 1991)

What is claimed is:

1. A synthetic gene encoding an insect-selective neurotoxin comprising a coding nucleotide sequence that has been optimized for gene expression based on codon bias of baculoviruses or of cells in which baculoviruses replicate wherein said synthetic gene comprises the nucleotide sequence of SEQ ID NO:12.

2. A synthetic gene comprising the synthetic gene of claim 1 fused in-frame to a nucleotide sequence encoding a suitable signal peptide.

3. A recombinant baculovirus comprising the synthetic gene of claim 1.

4. The synthetic gene of claim 2 wherein the suitable signal peptide is derived from bombyxin.

5. A chimeric gene comprising the synthetic gene of claim 2 operably linked to one or more regulatory sequences that direct expression of the coding sequences of the chimeric gene in an insect cell.

6. A recombinant baculovirus comprising the synthetic gene of claim 2.

7. The synthetic gene of claim 4 comprising the nucleotide sequence of SEQ ID NO:13.

8. The chimeric gene of claim 5 wherein the regulatory sequences comprise baculovirus promoters selected from the group of early promoters, immediately early promoters, late promoters, and very late promoters.

9. A recombinant baculovirus comprising the chimeric gene of claim 5.

10. The recombinant baculovirus of claim 9 selected from the group of recombinant baculoviruses designated by ATCC Accession Number ATCC VR-2501 and ATCC Accession Number ATCC VR-2502.

11. An insecticidal composition comprising a recombinant baculovirus according to any one of claims 3–10 and a suitable carrier therefor.

12. A method for controlling arthropods comprising applying to them or their environment an insecticidally effective amount of the recombinant baculovirus according to any one of claims 3–10.

* * * * *

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
      (A) LENGTH: 75 base pairs
      (B) TYPE: nucleic acid
      (C) STRANDEDNESS: single
      (D) TOPOLOGY: linear (ii) MOLECULE TYPE: DNA (artificial)

(xi) SEQUENCE DESCRIPTION: SEQ ID NO:1:

ACGATGAATT CGGATCCTAT GAAGATCCTC CTTGCTATTG CCCTTATGCT TAGCACCGTG    60

ATGTGGGTGA GCACC    75

(2) INFORMATION FOR SEQ ID NO:2:

(i) SEQUENCE CHARACTERISTICS:
      (A) LENGTH: 51 base pairs
      (B) TYPE: nucleic acid
      (C) STRANDEDNESS: single
      (D) TOPOLOGY: linear (ii) MOLECULE TYPE: DNA (artificial)

(xi) SEQUENCE DESCRIPTION: SEQ ID NO:2:

GACGGCTACA TCAAACGCCG CGACGGCTGC AAAGTGGCCT GCCTTATCGG C    51

(2) INFORMATION FOR SEQ ID NO:3:

(i) SEQUENCE CHARACTERISTICS:
      (A) LENGTH: 51 base pairs
      (B) TYPE: nucleic acid
      (C) STRANDEDNESS: single
      (D) TOPOLOGY: linear (ii) MOLECULE TYPE: DNA (artificial)

(xi) SEQUENCE DESCRIPTION: SEQ ID NO:3:

AACGAGGGCT GCGACAAAGA GTGCAAAGCC TACGGCGGCA GCTACGGCTA C    51

(2) INFORMATION FOR SEQ ID NO:4:

(i) SEQUENCE CHARACTERISTICS:
      (A) LENGTH: 51 base pairs
      (B) TYPE: nucleic acid
      (C) STRANDEDNESS: single
      (D) TOPOLOGY: linear (ii) MOLECULE TYPE: DNA (artificial)

(xi) SEQUENCE DESCRIPTION: SEQ ID NO:4:

TGCTGGACCT GGGGCCTCGC ATGCTGGTGC GAGGGCCTCC CCGACGACAA A  51

(2) INFORMATION FOR SEQ ID NO:5:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (artificial)

(xi) SEQUENCE DESCRIPTION: SEQ ID NO:5:

ACCTGGAAAA GCGAGACCAA CACCTGCGGC TAAGGATCCT CTAGAGTC  48

(2) INFORMATION FOR SEQ ID NO:6:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ii) MOLECULE TYPE: DNA (artificial)

(xi) SEQUENCE DESCRIPTION: SEQ ID NO:6:

CACCCACATC ACGGTGCTAA GCATAAGGGC AATAGCAAGG AGGATCTTCA TAGGATCCGA  60

ATTCATCGT  69

(2) INFORMATION FOR SEQ ID NO:7:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (artificial)

(xi) SEQUENCE DESCRIPTION: SEQ ID NO:7:

AAGGCAGGCC ACTTTGCAGC CGTCGCGGCG TTTGATGTAG CCGTCGGTGC T  51

(2) INFORMATION FOR SEQ ID NO:8:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (artificial)

(xi) SEQUENCE DESCRIPTION: SEQ ID NO:8:

GTAGCTGCCG CCGTAGGCTT TGCACTCTTT GTCGCAGCCC TCGTTGCCGA T  51

(2) INFORMATION FOR SEQ ID NO:9:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (artificial)

(xi) SEQUENCE DESCRIPTION: SEQ ID NO:9:

```
GTCGGGGAGG CCCTCGCACC AGCATGCGAG GCCCCAGGTC CAGCAGTAGC G              51
```

(2) INFORMATION FOR SEQ ID NO:10:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (artificial)

(xi) SEQUENCE DESCRIPTION: SEQ ID NO:10:

```
GACTCTAGAG GATCCTTAGC CGCAGGTGTT GGTCTCGCTT TTCCAGGTTT TGTC           54
```

(2) INFORMATION FOR SEQ ID NO:11:

(i) SEQUENCE CHARACTERISTICS:
        (A) LENGTH: 186 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

```
GACGGATATA TAAAAAGACG AGACGGATGC AAGGTTGCAT GCCTGATCGG AAATGAGGGC     60
TGCGATAAAG AATGCAAAGC TTATGGTGGC TCTTATGGAT ATTGTTGGAC CTGGGGACTT    120
GCCTGCTGGT GCGAAGGTCT TCCGGATGAC AAGACATGGA AGAGTGAAAC AAACACATGC    180
GGTTAA                                                               186
```

(2) INFORMATION FOR SEQ ID NO:12:

(i) SEQUENCE CHARACTERISTICS:
        (A) LENGTH: 186 base pairs
        (B) TYPE: nucleic acid
        (C) STRANDEDNESS: single
        (D) TOPOLOGY: linear (ii) MOLECULE TYPE: DNA (artificial)

(xi) SEQUENCE DESCRIPTION: SEQ ID NO:12:

```
GACGGCTACA TCAAACGCCG CGACGGCTGC AAAGTGGCCT GCCTTATCGG CAACGAGGGC     60
TGCGACAAAG AGTGCAAGGC CTACGGCGGC AGCTACGGCT ACTGCTGGAC CTGGGGCCTC    120
GCATGCTGGT GCGAGGGCCT CCCCGACGAC AAAAACCTGGA AAAGCGAAAC CAACACCTGC   180
GGCTAA                                                               186
```

(2) INFORMATION FOR SEQ ID NO:13:

(i) SEQUENCE CHARACTERISTICS:
        (A) LENGTH: 243 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

```
ATGAAGATCC TCCTTGCTAT TGCCCTTATG CTTAGCACCG TGATGTGGGT GAGCACCGAC     60
GGCTACATCA AACGCCGCGA CGGCTGCAAA GTGGCCTGCC TTATCGGCAA CGAGGGCTGC    120
GACAAAGAGT GCAAGGCCTA CGGCGGCAGC TACGGCTACT GCTGGACCTG GGGCCTCGCA    180
TGCTGGTGCG AGGGCCTCCC CGACGACAAA ACCTGGAAAA GCGAAACCAA CACCTGCGGC    240
```

```
                                                                    -continued

TAA                                                                     243

(2) INFORMATION FOR SEQ ID NO:14:

(i) SEQUENCE CHARACTERISTICS:
        (A) LENGTH:    80 amino acids
        (B) TYPE:      amino acid
        (C) STRANDEDNESS: single
        (D) TOPOLOGY:  linear (ii) MOLECULE TYPE:  protein (xi) SEQUENCE DESCRIPTION:  SEQ ID NO:14:

Met Lys Ile Leu Leu Ala Ile Ala Leu Met Leu Ser Thr Val Met Trp
 1               5                  10                  15

Val Ser Thr Asp Gly Tyr Ile Lys Arg Arg Asp Gly Cys Lys Val Ala
            20                  25                  30

Cys Leu Ile Gly Asn Glu Gly Cys Asp Lys Glu Cys Lys Ala Tyr Gly
        35                  40                  45

Gly Ser Tyr Gly Tyr Cys Trp Thr Trp Gly Leu Ala Cys Trp Cys Glu
        50                  55                  60

Gly Leu Pro Asp Asp Lys Thr Trp Lys Ser Glu Thr Asn Thr Cys Gly
65                  70                  75                  80
```